US010865171B1

(12) United States Patent
Boone

(10) Patent No.: US 10,865,171 B1
(45) Date of Patent: Dec. 15, 2020

(54) PROCESS TO MAKE AROMATIC ENOL ETHERS AND OLEFIN ISOMERS OF AROMATIC ENOL ETHERS

(71) Applicant: Eastman Chemical Company, Kingsport, TN (US)

(72) Inventor: Matthew Allen Boone, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/559,912

(22) Filed: Sep. 4, 2019

(51) Int. Cl.
| C07C 41/00 | (2006.01) |
| C07C 41/09 | (2006.01) |
| C07C 43/178 | (2006.01) |
| C07C 43/166 | (2006.01) |
| C07C 41/42 | (2006.01) |

(52) U.S. Cl.
CPC .............. *C07C 41/09* (2013.01); *C07C 41/42* (2013.01); *C07C 43/166* (2013.01); *C07C 43/1787* (2013.01)

(58) Field of Classification Search
CPC ........ C07C 41/09; C07C 41/42; C07C 43/166
See application file for complete search history.

(56) References Cited

U.S. PATENT DOCUMENTS

| 2,578,724 | A | 12/1951 | Mertzweiller |
| 4,839,413 | A | 6/1989 | Kiehlbauch et al. |
| 4,927,876 | A | 5/1990 | Coogan et al. |
| 4,939,233 | A | 7/1990 | Jenkins et al. |
| 4,946,932 | A | 8/1990 | Jenkins |
| 5,053,556 | A | 10/1991 | Ohnishi |
| 5,137,961 | A | 8/1992 | Goos et al. |
| 5,247,040 | A | 9/1993 | Amick et al. |
| 5,296,530 | A | 3/1994 | Bors et al. |
| 5,484,849 | A | 1/1996 | Bors et al. |
| 6,451,380 | B1 | 9/2002 | Speece, Jr. et al. |
| 6,743,748 | B2 | 6/2004 | Mizuno et al. |
| 7,208,545 | B1 | 4/2007 | Brunner et al. |
| 9,932,486 | B1 | 4/2018 | Cogar et al. |
| 2009/0035696 | A1 | 2/2009 | Matsuoka |
| 2009/0076311 | A1 | 3/2009 | Sato et al. |
| 2012/0289721 | A1 | 11/2012 | End et al. |
| 2015/0239816 | A1 | 8/2015 | Zaragoza Doerwald et al. |

FOREIGN PATENT DOCUMENTS

| EP | 0 492 847 A2 | 7/1992 |
| WO | WO 2007/094922 A2 | 8/2007 |

OTHER PUBLICATIONS

Co-pending U.S. Appl. No. 16/559,842, filed Sep. 4, 2019; Boone.
Co-pending U.S. Appl. No. 16/559,871, filed Sep. 4, 2019; Boone.
Co-pending U.S. Appl. No. 16/559,887, filed Sep. 4, 2019; Boone.
Co-pending U.S. Appl. No. 16/559,897, filed Sep. 4, 2019; Boone.
Co-pending U.S. Appl. No. 16/559,880, filed Sep. 4, 2019; Boone et al.
Co-pending U.S. Appl. No. 16/559,859, filed Sep. 4, 2019; Boone et al.
Co-pending U.S. Appl. No. 16/560,146, filed Sep. 4, 2019; Boone et al.
Co-pending U.S. Appl. No. 16/560,161, filed Sep. 4, 2019; Boone et al.
Co-pending U.S. Appl. No. 16/559,977, filed Sep. 4, 2019; Boone.
Co-pending U.S. Appl. No. 16/559,988, filed Sep. 4, 2019; Boone et al.
ASTM D1544; Standard Test Method for Color of Transparent Liquids (Gardner Color Scale).
ASTM D2354-10$^{e1}$; Standard Test Method for Minimum Film Formation Temperature (MFFT) of Emulsion Vehicles.
ASTM D4946; Standard Test Method for Blocking Resistance of Architectural Paints.
ASTM D6886; Standard Test Method for Determination of the Weight Percent Individual Volatile Organic Compounds in Waterborne Air-Dry Coatings by Gas Chromatography.
Burczyk, B. et al.; "Relations between chemical structure and surface activity I: Synthesis and properties of aqueous solutions of acetals formed from aliphatic aldehydes and monoalkyl ethers of ethylene glycols;" Tenside Detergents; 15(2); 1978; pp. 68-71.
Burczyk, B. et al.; "Surface Properties of Selected Linear and Cyclic Acetals;" Tensioactivos: Biodegradabilidad, Fis.-Quim. Apl., Jorn. Com. Esp. Deterg.; 11$^{th}$; 1980; pp. 581-601.
Cohen, R. et al.; "Foam stabilizing properties of linear acetals containing oxyethylene units in their molecules;" Tenside Detergents; 18 (4); 1981; pp. 202-205.
Duchene, A. et al.; "Alxoxyméthyltributylétains précurseurs d'alcoxyméthyllithiums : application à la synthèse de monoéthers d'α-glycols et à l'homologation de cétones en aldéhydes;" Bulletin De La Societe Chimique De France; 1985; No. 5; pp. 787-792.
Getzkin, AJ. et al.; "Synthesis of Some Symmetrical Aldehyde Glycol Monoether Acetals;" Journal of the American Pharmaceutical Association, Scientific Edition; 49; 1960; pp. 746-750.
Kanno, T. et al.; "Oxygenation of Aromatic Vinyl Ethers. A Noticeable Formation of Epoxides and Reaction Mechanism;" Bull. Chem. Soc. Jpn.; 54; 1981; pp. 2330-2336.
Moszner, N. et al.; "Reaction behavior of monomeric β-ketoesters. 2. Synthesis, characterization and polymerization of methacrylate group containing enamines;" Polymer Bulletin; 32; pp. 419-426; (1994).
Presidential Green Chemistry Challenge: 2005 Designing Greener Chemical Award; Archer Daniels Midland Company; Archer RC™: A Nonvolatile, Reactive Coalescent for the Reduction of VOCs in Latex Paints; United States Environmental Protection Agency; Accessed via the web on Jun. 6, 2018; https://www.epa.gov/greenchemistry/presidential-green-chemistry-challenge-2005-designing-greener-chemicals-award.

(Continued)

Primary Examiner — Sikarl A Witherspoon
(74) Attorney, Agent, or Firm — Matthew W. Smith

(57) ABSTRACT

Disclosed is a method for making aromatic enol ethers that have utility as film-hardening additives for coating formulations. The aromatic enol ethers have particular utility as film-hardening additives for water-based coating formulations. The aromatic enol ethers provide improvements in hardness and hardness related properties such as block resistance without contributing to the volatile organic content of the composition.

9 Claims, No Drawings

(56) References Cited

OTHER PUBLICATIONS

Robinson, M. et al.; "Epoxide ring-opening and Meinwald rearrangement reactions of epoxides catalyzed by mesoporous aluminosilicates;" Organic & Biomolecular Chemistry; 2009; 7; pp. 2559-2564.
Safa, K. et al.; "1,4-bis[2,2-bis(trimethylsilyl)ethenyl]benzene: Regioselective ring opening of its a,B-eposybix(silane) with some nucleophiles;" Journal of Organometallic Chemistry; 694; 20019; pp. 1907-1911.
Smith, O.W. et al.; "New vinyl ester monomers for emulsion polymers;" Progress in Organic Coatings; 22; 1993; pp. 19-25.
Sokolowski, A. et al.; "Acetals and Ethers. Part IV. Synthesis of Acetals from Aliphatic Aldehydes and Monoalkyl Ether of Ethylene Glycols;" Polish Journal of Chemistry (formerly Roczniki Chemii); 53(4); 1979; pp. 905-912.
Sokolowski, A. et al.; "Statistical Evaluation of the Influence of Linear Acetal Structures on Their Adsorption at the Aqueous Solution-Air Interface;" Comunicaciones presentadas a las XII Jornadas del Comite Espanol de la Detergencia; Asociacion De Investigacion De Detergentes, Tens; 1981; pp. 491-507.
USPTO Office Action dated Apr. 6, 2020 received in co-pending U.S. Appl. No. 16/559,842.
USPTO Notice of Allowance dated Nov. 1, 2019 received in co-pending U.S. Appl. No. 16/559,977.
USPTO Notice of Allowance dated Dec. 10, 2019 received in co-pending U.S. Appl. No. 16/559,977.
USPTO Notice of Allowance dated Nov. 1, 2019 received in co-pending U.S. Appl. No. 16/559,988.
USPTO Notice of Allowance dated Dec. 11, 2019 received in co-pending U.S. Appl. No. 16/559,988.
Kluge et al.; "Phosphonate Reagents for the Synthesis of Enol Ethers and One-Carbon Homologation to Aldehydes;" J. Org. Chem.; vol. 44; No. 26; 1979; pp. 4847-4852.
USPTO Office Action dated Apr. 30, 2020 received in co-pending U.S. Appl. No. 16/560,161.
Trost et al.; "Model for Asymmetric Induction in the Diels-Alder Reaction;" Journal of the American Chemical Society; vol. 102; 1980; pp. 7595-7596.
USPTO Office Action dated Jun. 1, 2020 received in co-pending U.S. Appl. No. 16/559,897.
USPTO Office Action dated Jun. 10, 2020 received in co-pending U.S. Appl. No. 16/559,871.
USPTO Notice of Allowance dated Jun. 24, 2020 received in co-pending U.S. Appl. No. 16/559,887.
USPTO Notice of Allowance dated Aug. 10, 2020 received in co-pending U.S. Appl. No. 16/559,842.
USPTO Notice of Allowance dated Aug. 17, 2020 received in co-pending U.S. Appl. No. 16/560,161.

PROCESS TO MAKE AROMATIC ENOL ETHERS AND OLEFIN ISOMERS OF AROMATIC ENOL ETHERS

FIELD OF THE INVENTION

This application relates to chemistry in general. In particular, this application relates to enol ethers and olefin isomers thereof and to an epoxide-opening, dehydration process to make enol ethers and olefin isomers thereof.

BACKGROUND OF THE INVENTION

Enol ethers are useful in a variety of chemical applications such as diluents, wetting agents and paint additives and as intermediates in chemical processes. Diluents, wetting agents and paint additives often are volatile and evaporate into the atmosphere during use. For example, coalescing aids that are added to water-based paints, act as temporary plasticizers in latex emulsions. The coalescing aids lowers the glass transition temperature (Tg) of the latex polymer and as the paint dries, the polymers that have been softened by the coalescing aid are allowed to flow together and form a film after the water has left the system. Coalescing aids that are volatile evaporate out of the film. This allows the polymer to return to the original Tg thereby giving harder films for better block and print resistant coatings.

Due to environmental concerns, the use of volatile materials such as paint additives, diluents, wetting agents and coalescing aids are increasing undesirable. There is a need for materials that can be used as diluents, wetting agents and paint additives that exhibit low volatility.

Enol ethers are traditionally synthesized in a two-stage fashion by contacting an aldehyde with an alcohol in the presence of an acid catalyst to generate an intermediate acetal, which can be thermally cracked to generate the product (Scheme 1). Typically, this equilibrium transformation is carried out in a refluxing solvent that forms an azeotrope with water (e.g. toluene) so that the water formed during the condensation can be removed thereby pushing the equilibrium to form the desired product.

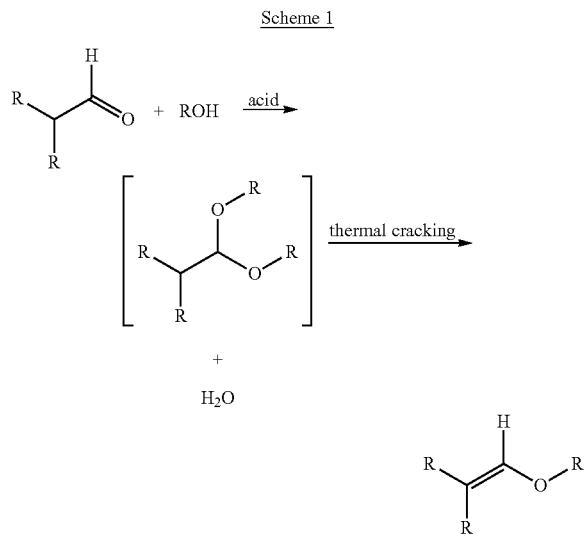

Scheme 1

The downside to this approach lies in the difficulty of suppressing color-formation both in the aldehyde condensation to form the acetal but especially in the thermal cracking stage of the process. In the synthesis of non-volatile small molecules used in coatings formulations, the boiling points of these materials can exceed 350° C., so this thermal cracking operation is further complicated, especially since final product color is commonly identified as critical-to-quality for coatings additives. Therefore, milder processes for forming enol ethers are of interest.

One such approach involves the base-catalyzed opening of an epoxide with an alcohol to form an ether-alcohol intermediate, followed by dehydration to produce an enol ether (Scheme 2). The advantage of this alternative approach lies in the low temperature (50°-65° C.) base-catalyzed opening of the epoxide and very mild (50°-65° C.) conditions for acid-catalyzed dehydration.

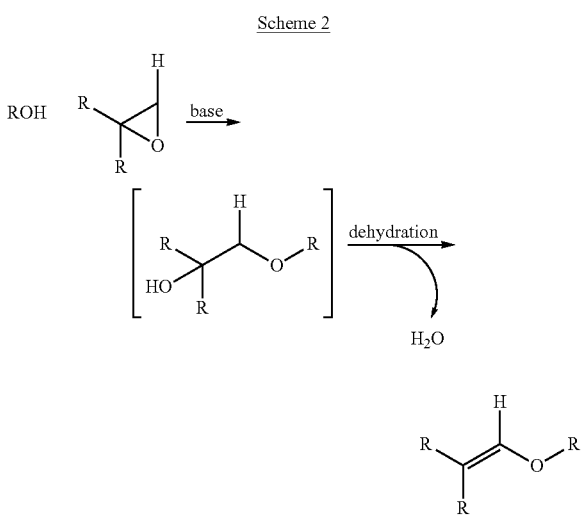

Scheme 2

While acid-catalyzed dehydration of alcohols to generate olefins is usually considered a trivial transformation, in the context of enol ether formation, the dehydration is more complicated (Scheme 3). Namely, when water is generated via the acid-catalyzed reaction, the enol ether that is formed can further react if water is not removed from the reaction mixture (it is important to note that traditional Dean-Stark removal of water using an azeotroping solvent at reflux is not adequate). This reaction of water with the enol ether engages competing equilibria reactions and the parent aldehyde can be produced, which in turn liberates free ROH. The free alcohol can then react with enol ether to produce an acetal. Without effective water removal, the generation of the aldehyde and acetal intermediates prolongs the reaction, as additional time is then needed to drive the reaction equilibrium back to the desired enol ether. This, in effect, voids the intended benefits of avoiding the use of the aldehyde process to produce an enol ether.

Scheme 3

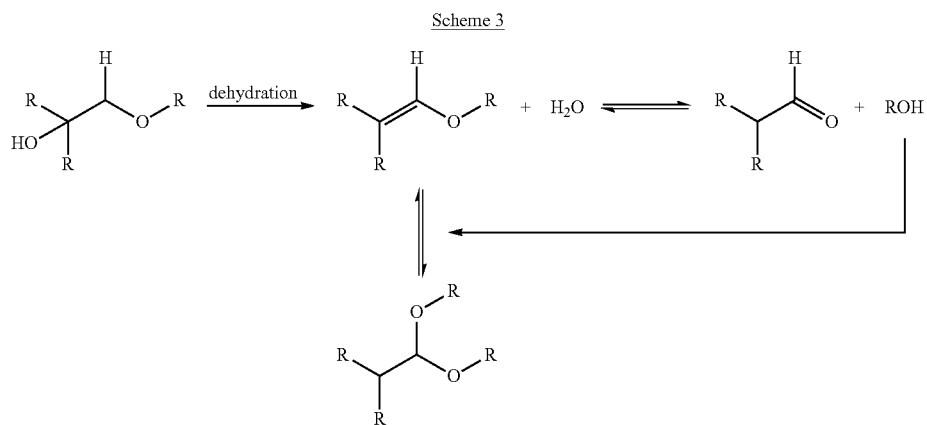

One method of addressing such an issue is to carry out the dehydration reaction in the presence of an additive or solvent that acts as a desiccant, through physical adsorption of the produced water or by sequestration of water through a chemical transformation. There are many drying agents known to one skilled in the art (i.e. sodium sulfate, magnesium sulfate, zeolite-based molecular sieves).

However, it is preferred to carry out the dehydration in the presence of a molecule that is water-reactive. One such option is an anhydride and it is preferred that acetic anhydride is used (Scheme 4). This method allows for very fast reaction times and superior control of selectivity (i.e. no evidence of acetal formation).

Scheme 4

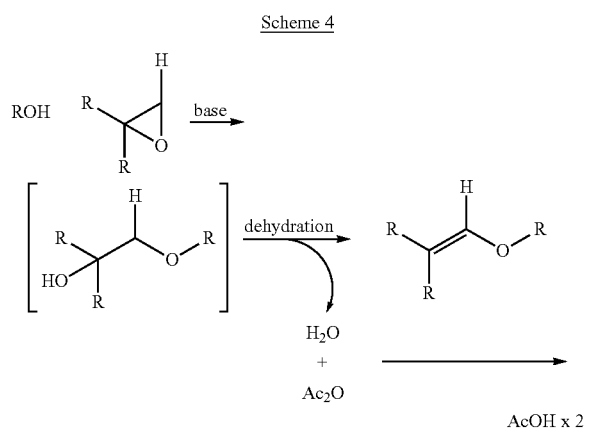

When the alcohol is attached to a carbon bearing an alkyl substituent bearing a hydrogen (i.e. methyl group), the regioselectivity of dehydration can be altered to produce both the enol ether and its 1,1-disubstituted olefin isomer. The ratio of enol ether to the 1,1-disub olefin can be influenced by the choice and amount of acid catalyst used in the dehydration reaction. If desired, there are numerous methods of olefin isomerization to convert the 1,1-disub olefin to the enol ether.

Scheme 5

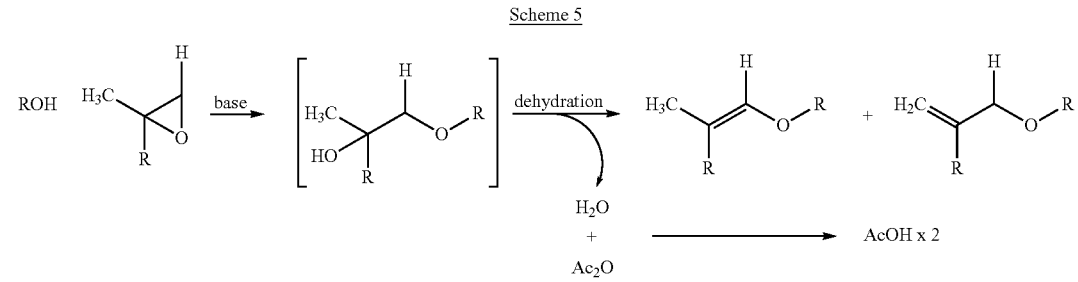

SUMMARY OF THE INVENTION

The invention is set forth in the appended claims.

The present application relates to a method of making aromatic enol ethers comprising:

a) contacting a glycol ether with a di-epoxide in the presence of a base to form a first reaction product;

b) combining said first reaction product with an aromatic hydrocarbon and an organic acid to form a second reaction product having an aqueous phase and a non-aqueous phase;

c) Separating said second reaction product aqueous phase from said second reaction product non-aqueous second phase;

d) drying said second reaction product non-aqueous phase to recover a dicarbinol;

e) dehydrating said dicarbinol with an acid catalyst to form a mixture of an aromatic enol ether and water; and f) separating said aromatic ether from said water.

In some embodiments the invention is an enol ether composition having Formula II, II or IV:

wherein Formula II is

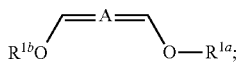

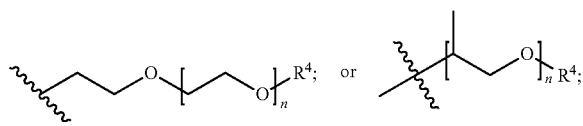

A is $(C_{8-20})$alkylaryl; $R^{1a}$ and $R^{1b}$ are independently each $R^4$ is independently hydrogen, $(C_{1-12})$alkyl, $(C_{2-12})$alkenyl or $-C(O)R^5$; each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; $R^6$ is $(C_{1-4})$alkoxy, or oxo; and each n is independently an integer from 1 to 15;
Formula III is

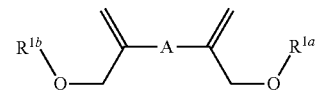

A is $(C_{8-20})$alkylaryl; $R^{1a}$ and $R^{1b}$ are independently

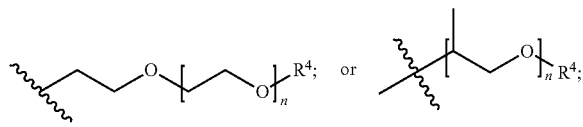

each $R^4$ is independently hydrogen, $(C_{1-12})$alkyl, $(C_{2-12})$alkenyl or $-C(O)R^5$; each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; $R^6$ is $(C_{1-4})$alkoxy, or oxo; and each n is independently an integer from 1 to 15 and
Formula IV is

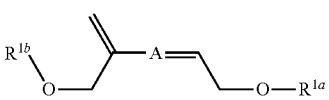

A is $(C_{8-20})$alkylaryl; $R^{1a}$ and $R^{1b}$ are independently

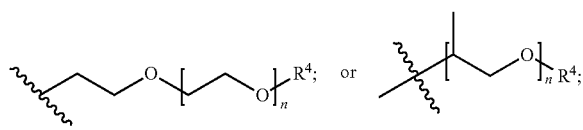

each $R^4$ is independently hydrogen, $(C_{1-12})$alkyl, $(C_{2-12})$alkenyl or $-C(O)R^5$; each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; $R^6$ is $(C_{1-4})$alkoxy, or oxo; and each n is independently an integer from 1 to 15.

DETAILED DESCRIPTION

Definitions

In this specification and in the claims that follow, reference will be made to a number of terms, which shall be defined to have the following meanings.

"Alkyl" means an aliphatic hydrocarbon. The alkyl can specify the number of carbon atoms, for example $(C_{1-5})$alkyl. Unless otherwise specified, the alkyl group can be unbranched or branched. In some embodiments, the alkyl group is branched. In some embodiments, the alkyl group is unbranched. Non-limiting examples of alkanes include methane, ethane, propane, isopropyl (i.e., branched propyl), butyl, and the like.

"Alkenyl" means an aliphatic hydrocarbon with one or more unsaturated carbon-carbon bonds. The alkenyl can specify the number of carbon atoms, for example $(C_{2-12})$alkenyl. Unless otherwise specified, the alkyl group can be unbranched or branched. In some embodiments, the alkyl group is branched. In some embodiments, the alkyl group is unbranched. Non-limiting examples of alkanes include ethynyl, propenyl, butenyl, hexa-3,5-dienyl, and the like.

"Alcohol" means a chemical containing one or more hydroxyl groups.

"Aldehyde" means a chemical containing one or more $-C(O)H$ groups.

"Cycloalkyl" means a cyclic hydrocarbon compound. The cycloalkyl can specify the number of carbon atoms in ring system, for example $(C_{3-8})$cycloalkyl. Non-limiting examples of cycloalkyl include cyclopropyl, cyclobutyl, cyclohexyl, and cyclooctyl.

"Aryl" means a ring system made up carbon atoms that has at least one ring that is aromatic. The carbon units making up the aryl ring may be specified, for example 5- to 9-membered aryl. Non-limiting examples of aryl include phenyl, naphthyl, 2,3-dihydro-1H-indene, and 1,2,3,4-tetrahydronaphthalene.

Values may be expressed as "about" or "approximately" a given number. Similarly, ranges may be expressed herein as from "about" one particular value and/or to "about" or another particular value. When such a range is expressed, another aspect includes from the one particular value and/or to the other particular value. Similarly, when values are expressed as approximations, by use of the antecedent "about," it will be understood that the particular value forms another aspect.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

"Chosen from" as used herein can be used with "or" or "and." For example, Y is chosen from A, B, and C means Y can be individually A, B, or C. Alternatively, Y is chosen from A, B, or C means Y can be individually A, B, or C; or a combination of A and B, A and C, B and C, or A, B, and C.

As used herein numerical ranges are intended to include the beginning number in the range and the ending number in the range and all numerical values and ranges in between the beginning and ending range numbers. For example, the range 40° C. to 60° C. includes the ranges 40° C. to 59° C., 41° C. to 60° C., 41.5° C. to 55.75° C. and 40°, 41°, 42°, 43°, etc. through 60° C.

Presented herein is a method for making novel enol ethers which can be used in applications such as (but not limited to) diluents, wetting agents, coalescing aids and paint additives.

The method comprises:
1) contacting a glycol ether with a di-epoxide in the presence of a base to form a first reaction product;
2) combining said first reaction product with an aromatic hydrocarbon and an organic acid to form a second reaction product having an aqueous phase and a non-aqueous phase;
3) Separating said second reaction product aqueous phase from said second reaction product non-aqueous second phase;
4) drying said second reaction product non-aqueous phase to recover a dicarbinol;
5) dehydrating said dicarbinol with an acid catalyst to form a mixture of an aromatic enol ether and water; and
6) separating said aromatic ether from said water.

Suitable glycol ethers for this method include ethylene glycol monomethyl ether, ethylenene glycol monoethyl ether, ethylene glycol monopropyl ether, ethylene glycol monobutyl ether, diethylene glycol monomethyl ether, diethylene glycol monoethyl ether, diethylene glycol monopropyl ether, diethylene glycol monoisopropyl ether, diethylene glycol monobutyl ether, triethylene glycol monomethyl ether, triethylene glycol monoethyl ether, triethylene glycol monopropyl ether, triethylene glycol monobutyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, dipropylene glycol monopropyl ether, dipropylene glycol monobutyl ether, tripropylene glycol monomethyl ether, tripropylene glycol monoethyl ether, tripropylene glycol monopropyl ether, tripropylene glycol monobutyl ether, or mixtures thereof.

Preferred glycol ethers for this method are ethylene glycol monobutyl ether, diethylene glycol monomethyl ether, diethylene glycol monoethyl ether, diethylene glycol monopropyl ether, diethylene glycol monoisopropyl ether, diethylene glycol monobutyl ether, triethylene glycol monomethyl ether, triethylene glycol monobutyl ether, dipropylene glycol monomethyl ether, tripropylene glycol monomethyl ether or mixtures thereof.

Di-epoxides suitable for use in this method include 1,3-bis(2-methyloxiran-2-yl)benzene, 1,4-bis(2-methyloxiran-2-yl)benzene, 1,3-di(oxiran-2-yl)benzene, 1,4-di(oxiran-2-yl)benzene 4,4'-bis(2-methyloxiran-2-yl)-1,1'-biphenyl, and 2,6-bis(2-methyloxiran-2-yl)naphthalene or mixtures thereof.

Preferred di-epoxides for use in this method are 1,3-bis (2-methyloxiran-2-yl)benzene, 1,4-bis(2-methyloxiran-2-yl)benzene or mixtures thereof.

Suitable basic materials for use in step 1 include sodium hydroxide, potassium hydroxide, lithium hydroxide, sodium metal, sodium methoxide, potassium tert-butoxide, anion exchange resins and combinations or mixtures thereof.

Preferred basic materials for use in step 1 include sodium hydroxide, potassium hydroxide, and sodium methoxide or mixtures thereof.

Aromatic hydrocarbons suitable for use in this method include toluene, chlorobenzene, para-xylene, meta-xylene, and ortho-xylene or mixtures thereof.

Preferred aromatic hydrocarbons are toluene and chlorobenzene or mixtures thereof.

Suitable acids for use in this method include cationic exchange resins (e.g. Amberlyst 15, Nafion NR50), sulfuric acid, phosphoric acid, hydrochloric acid, formic acid, and acetic acid or mixtures thereof.

Preferred acids are sulfuric acid, phosphoric acid, hydrochloric acid, and acetic acid or mixtures thereof.

Suitable separation techniques for step 3 include liquid-liquid extraction.

Suitable drying techniques for step 4 include filtration through a desiccant bed, azeotropic distillation with heptane, toluene, or xylene to remove trace water and combinations thereof.

Suitable acid catalysts for Step 6 include para-toluene sulfonic acid, methane sulfonic acid, camphor sulfonic acid, cationic exchange resins (e.g. Amberlyst 15, Nafion NR50), sulfuric acid, phosphoric acid, hydrochloric acid, formic acid, chloroacetic acid, dichloroacetic acid, trichloroacetic acid, trifluoroacetic acid, sodium hydrogen sulfate, potassium hydrogen sulfate and mixtures thereof.

Suitable separation techniques for step 7 include distillation or extraction or a combination thereof.

Step a) of the process wherein a glycol ether is contacted with a di-epoxide in the presence of a base can be conducted at a temperature of 40° C. to 80° C., or 40° C. to 75° C., or 40° C. to 70° C., or 40° C. to 65° C., or 40° C. to 60° C., or 45° C. to 55° C., or any temperature within the aforementioned ranges. It is preferable to maintain the temperature below about 80° C. to avoid discoloration of the first reaction product.

The dicarbinol material that is dehydrated to the aromatic enol ethers in this method are represented by Formula I:

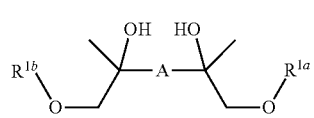

wherein: A is $(C_{8-20})$alkylaryl; $R^{1a}$ and $R^{1b}$ are independently

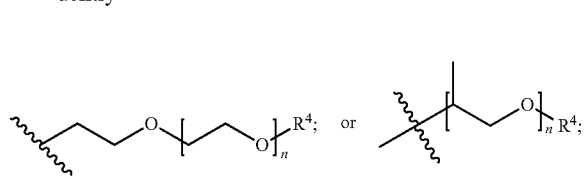

each $R^4$ is independently hydrogen, $(C_{1-12})$alkyl, $(C_{2-12})$alkenyl or —C(O)$R^5$; each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; $R^6$ is $(C_{1-4})$alkoxy, or oxo; and each n is independently an integer from 1 to 15.

In some embodiments of this invention, the aromatic enol ethers produced by this method are represented by Formulas II, III, and IV.

In some embodiments Formula II is

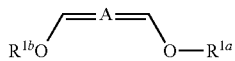

II wherein: A is $(C_{8-20})$alkylaryl; $R^{1a}$ and $R^{1b}$ are independently

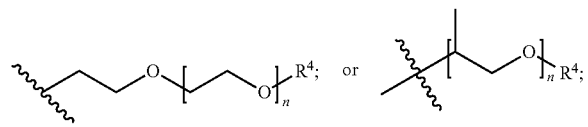

each $R^4$ is independently hydrogen, $(C_{1-12})$alkyl, $(C_{2-12})$alkenyl or —C(O)$R^5$; each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; $R^6$ is $(C_{1-4})$alkoxy, or oxo; and each n is independently an integer from 1 to 15.

In some embodiments Formula III is

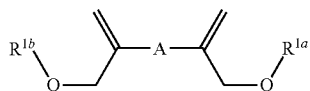

III wherein: A is $(C_{8-20})$alkylaryl; $R^{1a}$ and $R^{1b}$ are independently

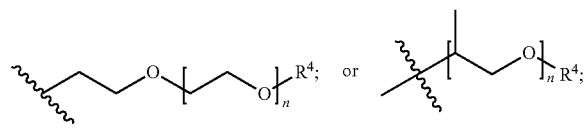

each $R^4$ is independently hydrogen, $(C_{1-12})$alkyl, $(C_{2-12})$alkenyl or —C(O)$R^5$; each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; $R^6$ is $(C_{1-4})$alkoxy, or oxo; and each n is independently an integer from 1 to 15.

In some embodiments Formula IV is

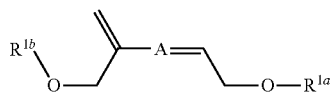

IV wherein: A is $(C_{8-20})$alkylaryl; $R^{1a}$ and $R^{1b}$ are independently

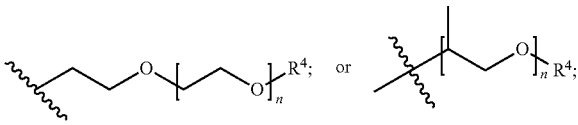

each $R^4$ is independently hydrogen, $(C_{1-12})$alkyl, $(C_{2-12})$alkenyl or —C(O)$R^5$; each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; $R^6$ is $(C_{1-4})$alkoxy, or oxo; and each n is independently an integer from 1 to 15.

In some embodiments, A in Formulas II, III and IV, is 1,2-, 1,3-, or 1,4-disubstituted phenyl. In some embodiments, each n is an integer from 1 to 3.

In some embodiments of Formulas II, III and IV, each $R^4$ is hydrogen. In some embodiments, each $R^4$ is $(C_{1-12})$alkyl. In some embodiments, each $R^4$ is independently ethyl. In some embodiments, each $R^4$ is (C2-12)alkenyl. In some embodiments, each $R^4$ is —C(O)$R^5$.

In some embodiments of Formulas II, III and IV, each $R^5$ is $(C_{1-12})$alkyl unsubstituted or substituted by $R^6$. In some embodiments, each $R^5$ is $(C_{1-12})$alkenyl unsubstituted or substituted by $R^6$. In some embodiments, each $R^5$ is $(C_{3-8})$cycloalkyl. In some embodiments, each $R^5$ is 5- to 9-membered aryl.

In some embodiments of Formulas II, III and IV, each n is an integer from 1 to 2. In some embodiments, each n is an integer from 1 to 3. In some embodiments, each n is an integer from 1 to 4. In some embodiments, each n is an integer from 1 to 5. In some embodiments, n is an integer from 1 to 6. In some embodiments, n is an integer from 1 to 7. In some embodiments, n is an integer from 1 to 8. In some embodiments, n is an integer from 1 to 9. In some embodiments, n is an integer from 1 to 10. In some embodiments, n is an integer from 1 to 11. In some embodiments, n is an integer from 1 to 12. In some embodiments, n is an integer from 1 to 13. In some embodiments, n is an integer from 1 to 14. In some embodiments, n is an integer from 1 to 15.

In some embodiments, the compounds of Formulas II, III and IV have a volatile organic content of less than 50 wt % according to ASTM D6886. In some embodiments, the volatile organic content is less than 30 wt %. In some embodiments, the volatile organic content is less than 10 wt %. In some embodiments, the volatile organic content is less than 5 wt %. In some embodiments, the volatile organic content is less than 3 wt %. In some embodiments, the volatile organic content is less than 2 wt %. In some embodiments, the volatile organic content is less than 1 wt %. In some embodiments, the volatile organic content is less than 0.8 wt %.

Compositions

The compounds disclosed in the present application exhibit a low volatile organic content (less than 50 wt %, but as low as 0.7 wt % according to ASTM D6886) and are reactive film-hardening compounds. Reactive film-hardening compounds react with components in coating compositions to form crosslinks in the films providing improved film properties. When we say that the compounds of this invention are reactive film-hardening additives, we mean when added to a coating composition, that a harder film is obtained upon curing the composition than is obtained in the absence of the invention additives, or that the coating composition exhibits a higher gel fraction than in the absence of the invention additive, or that both coating composition hardness and increased gel fraction properties are improved by the addition of the invention reactive film-hardening additives.

Not wishing to be bound by any theory, the increase in hardness observed and described herein for these reactive film-hardening additives appears to result from a chemical reaction, so that the additives described herein may be described as "reactive additives". These materials facilitate the individual latex particles coming together to form a continuous film at a given temperature by reducing the minimum film-forming temperature (MFFT) of the latex polymer. As used herein, the compounds of the invention (i.e., Formulas II, III and IV) act as reactive film-hardening additives by reducing the minimum film-forming temperatures of the coating compositions in which they are used.

In some embodiments, the composition comprises the compounds represented by Formulas II, III and IV.

In some embodiments, the compounds of Formula II, III and IV are enol ethers represented by Formulas 5-20.

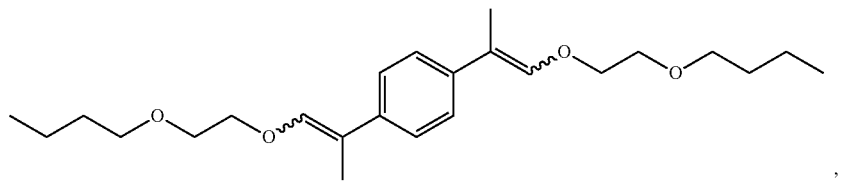

5

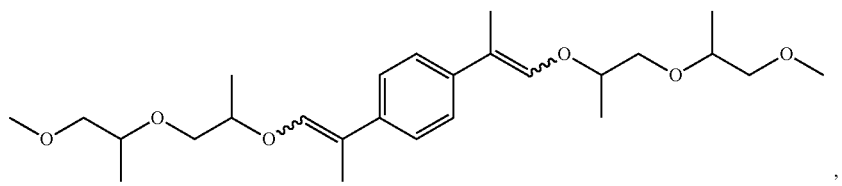

6

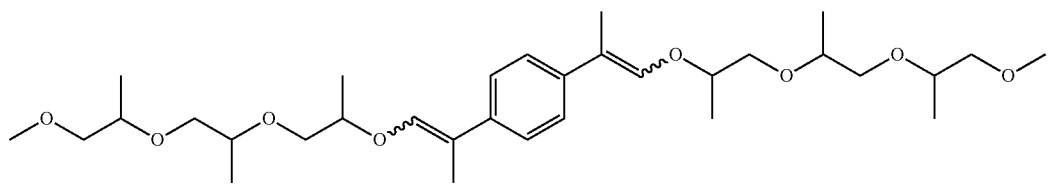

7

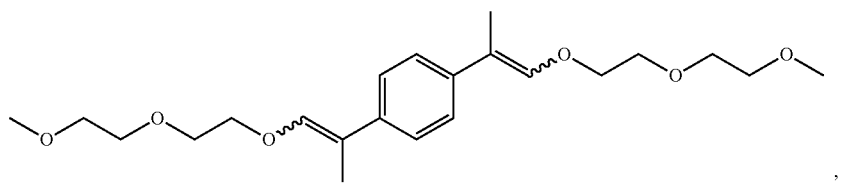

8

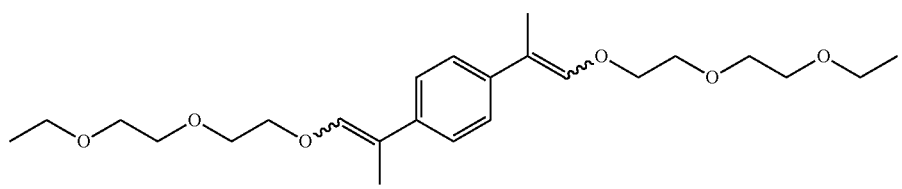

9

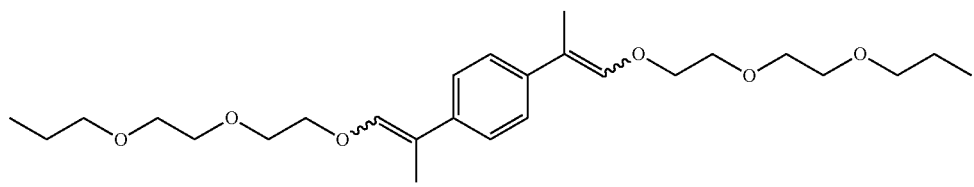

10

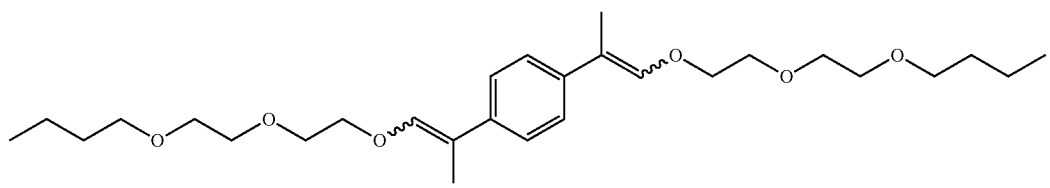

11

-continued
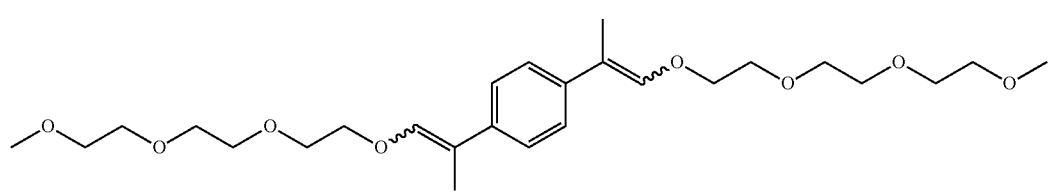
12
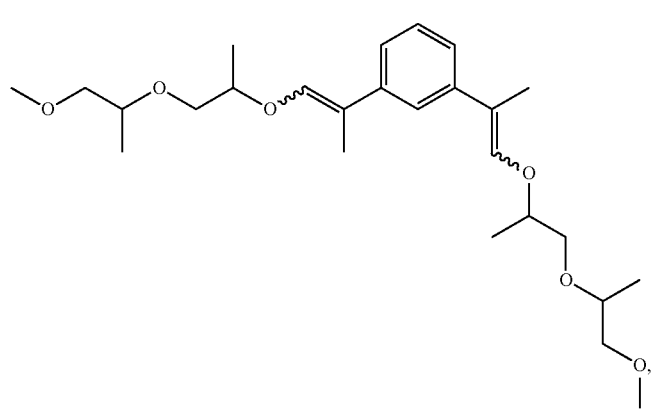
13
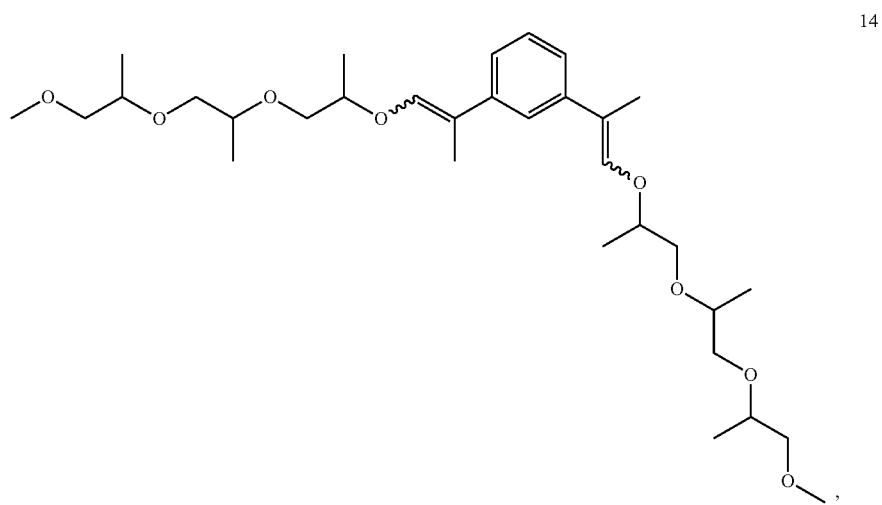
14
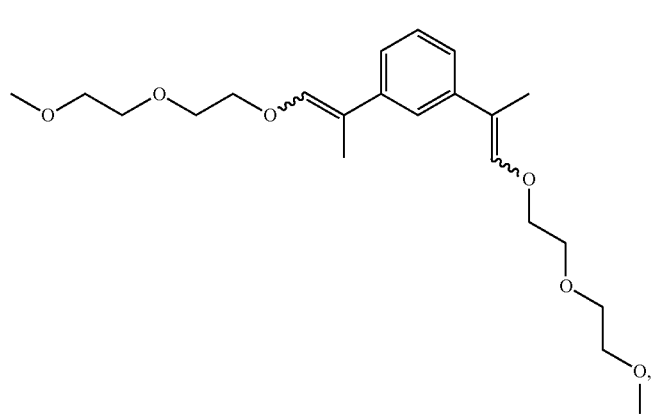
15

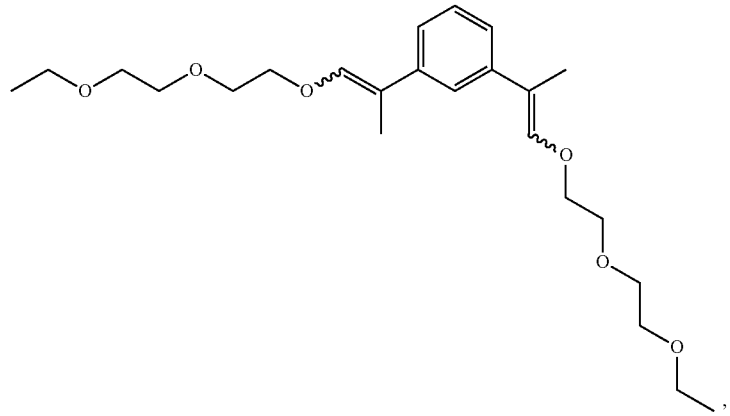
16
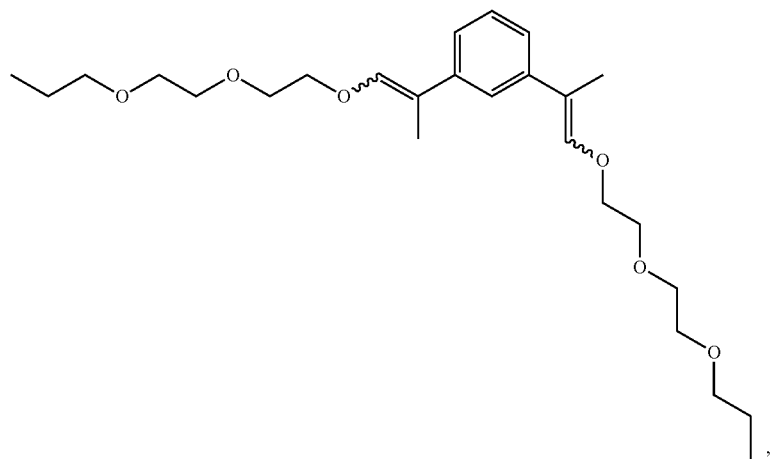
17
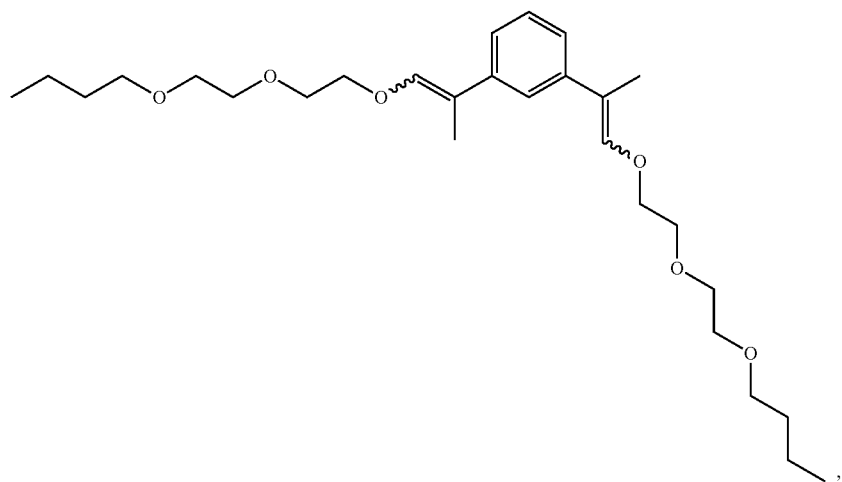
18

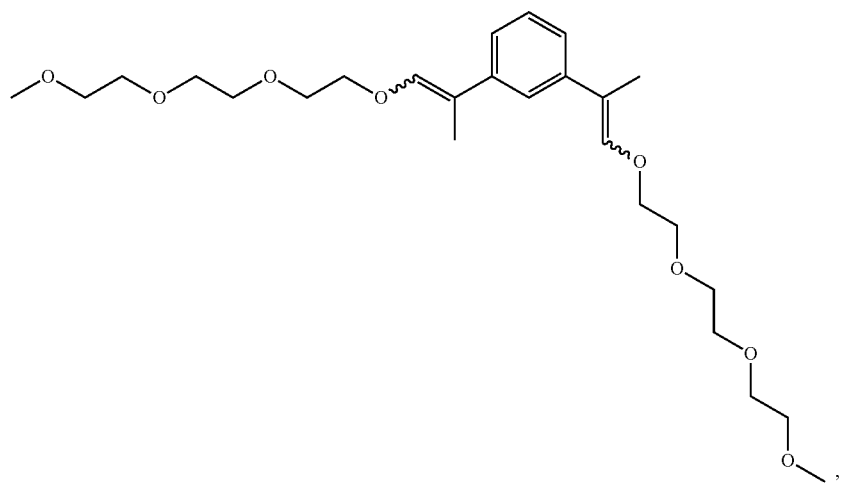

The enol ethers depicted by Formulas 5-19 are representative of the enol ethers claimed herein. Isomers of the enol ethers depicted by Formulas 5-19 are expected to be produced during synthesis of the enol ethers depicted by Formulas 5-19. All isomers of the enol ethers depicted by Formulas 5-19 and are within the scope of the claims set forth herein. Representative isomers are described in the examples herein below.

The compounds depicted by Formulas II, III and IV of the present invention include those having a weight percent volatile content of less than 50%, as measured according to ASTM Method D6886. This test may be conducted generally by heating the sample in a forced air oven at 110° C. for 60 minutes. The weight loss after the test is deemed to result from a loss of volatiles originally present in the sample; the percent volatile present in the original sample may then be calculated. Although the cited test can be conducted on coating compositions containing other components such as latex polymers, the values cited herein may be obtained from a sample of the additive itself. The weight percent volatile of a film-hardening aid may be used herein as a yardstick to measure the amount of VOC the additive would contribute to the VOC in a particular end use such as a component of a coating composition.

EXAMPLES

This invention can be further illustrated by the following examples thereof, although it will be understood that these examples are included merely for purposes of illustration and are not intended to limit the scope of the invention unless otherwise specifically indicated.

Abbreviations mL is milliliter; wt % is weight percent; eq is equivalent(s); hrs. or h is hour(s); mm is millimeter; m is meter; GC is gas chromatography; ° C. is degree Celsius; min is minute; $t_R$ is retention time; VOC is volatile organic compound; MeP is methyl palmitate; w/v is weight/volume; μL is microliter. RFHA is reactive film-hardening additive.

General Procedure for Epoxide Opening

To a 4-necked round-bottom flask fitted with thermocouple, nitrogen inlet, and overhead stirrer was added glycol ether (5 equiv.). Then the di-epoxide was added all at once. The mixture was heated to an internal temperature of 50° C. (note: the 1,4-di-epoxide is a solid that requires some additional time for dissolution; the 1,3-di-epoxide is a liquid at room temperature). The KOH (90%, flakes, 2 equiv.) was added portion-wise such that the internal temperature did not exceed 70° C., over the course of 1 to 1.5 hrs. Once the addition of base was complete, the reaction was monitored by $^1$H NMR (aliquot was dissolved in DMSO-$d_6$). After the di-epoxide was completely consumed, the mixture was cooled to room temperature. The mixture was then poured into ice water. Toluene was added to the mixture and then acetic acid (2.05 equiv. was added). The mixture was transferred to a separatory funnel. After layer separation, the aqueous layer was back-extracted with ethyl acetate. The organics were combined and dried with MgSO$_4$, while stirring with activated carbon. The mixture was filtered, and the volatiles were removed using a rotary evaporator. Kugelrohr distillation was used to remove excess glycol ether, if needed.

Example 1: Preparation of 2,2'-(1,4-phenylene)bis(1-((1-((1-methoxypropan-2-yl)oxy)propan-2-yl)oxy)propan-2-ol) [22]

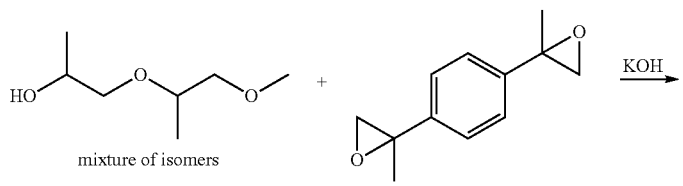

mixture of isomers

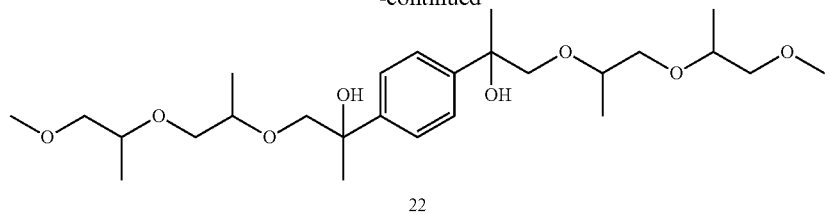
22
LC-MS $t_R$: 6.46 min (Exact mass: 486.32 m/z, found: 486.3 m/z).
Example 2: Preparation of 13,13'-(1,4-phenylene) bis(4,7,10-trimethyl-2,5,8,11-tetraoxatetradecan-13-ol) [23]
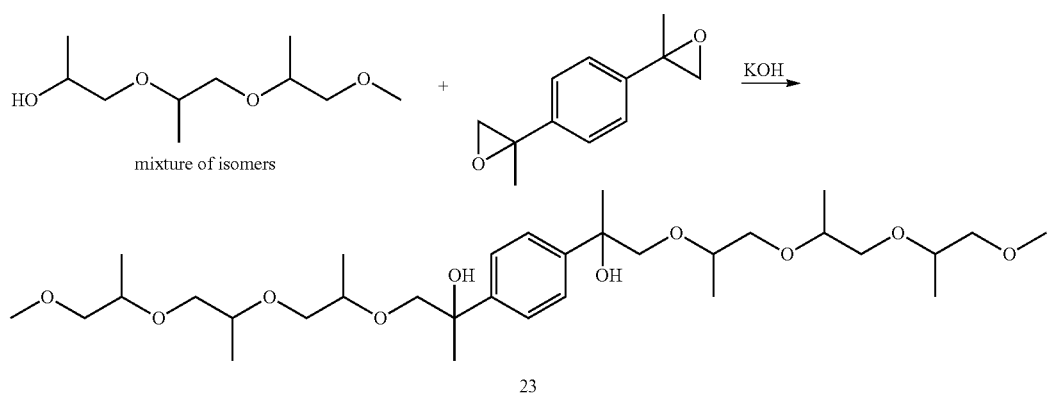
23
LC-MS $t_R$: 7.54 min (Exact mass: 602.40 m/z, found: 602.4 m/z).
Example 3: Preparation of 2,2'-(1,4-phenylene)bis (1-(2-(2-methoxyethoxy)ethoxy)propan-2-ol) [24]
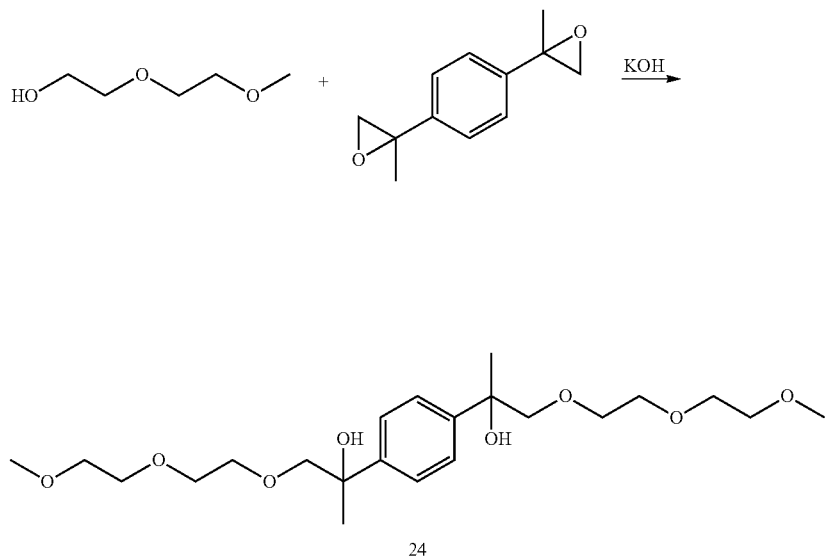
24
LC-MS $t_R$: 4.44 min (Exact mass: 430.26 m/z, found: 430.3 m/z).

Example 4: Preparation of 2,2'-(1,4-phenylene)bis(1-(2-(2-ethoxyethoxy)ethoxy)propan-2-ol) [25]
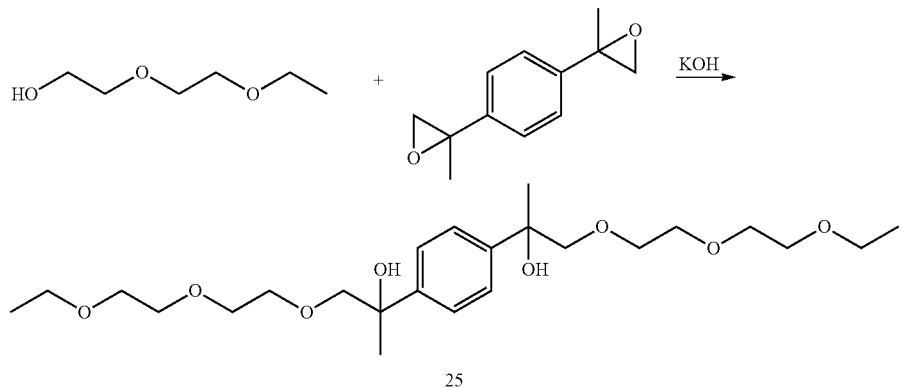
25
LC-MS $t_R$: 5.32 min (Exact mass: 458.29 m/z, found: 458.3 m/z).
Example 5: Preparation of 2,2'-(1,4-phenylene)bis(1-(2-(2-propoxyethoxy)ethoxy)propan-2-ol) [26]
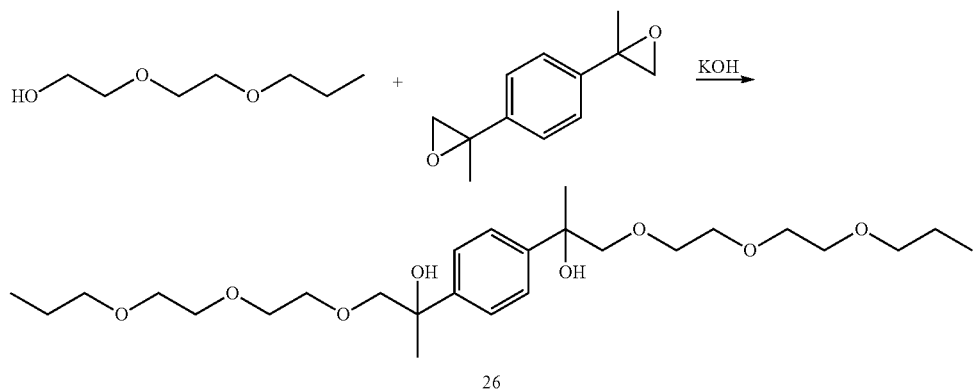
26
LC-MS $t_R$: 6.46 min (Exact mass: 486.32 m/z, found: 486.3 m/z).
Example 6: Preparation of 2,2'-(1,4-phenylene)bis(1-(2-(2-butoxyethoxy)ethoxy)propan-2-ol) [27]
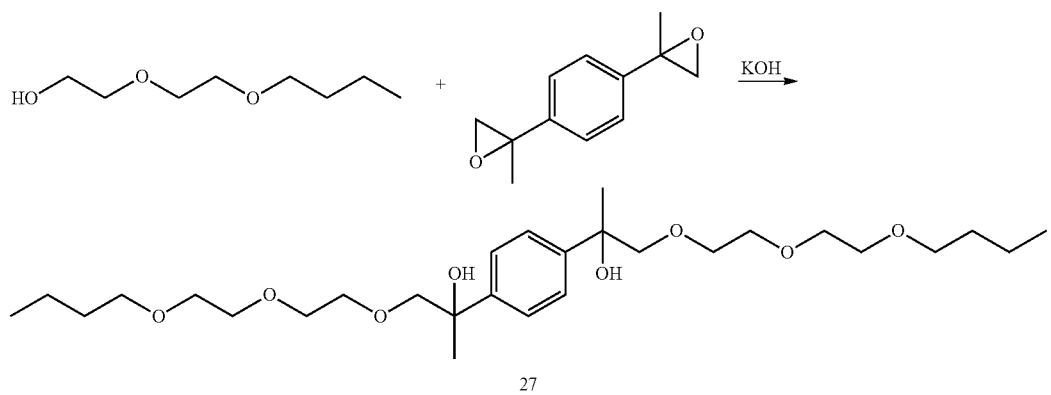
27
LC-MS $t_R$: 7.60 min (Exact mass: 514.35 m/z, found: 514.4 m/z).

Example 7: Preparation of 13,13'-(1,4-phenylene)
bis(2,5,8,11-tetraoxatetradecan-13-ol) [28]
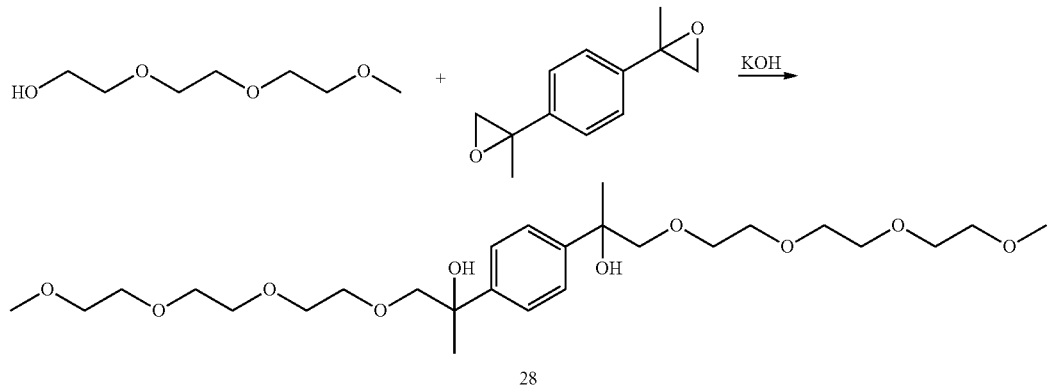
LC-MS $t_R$: 4.62 min (Exact mass: 518.31 m/z, found: 518.3 m/z).
Example 8: Preparation of 2,2'-(1,4-phenylene)bis
(4,7,10,13-tetraoxaheptadecan-2-ol) [29]
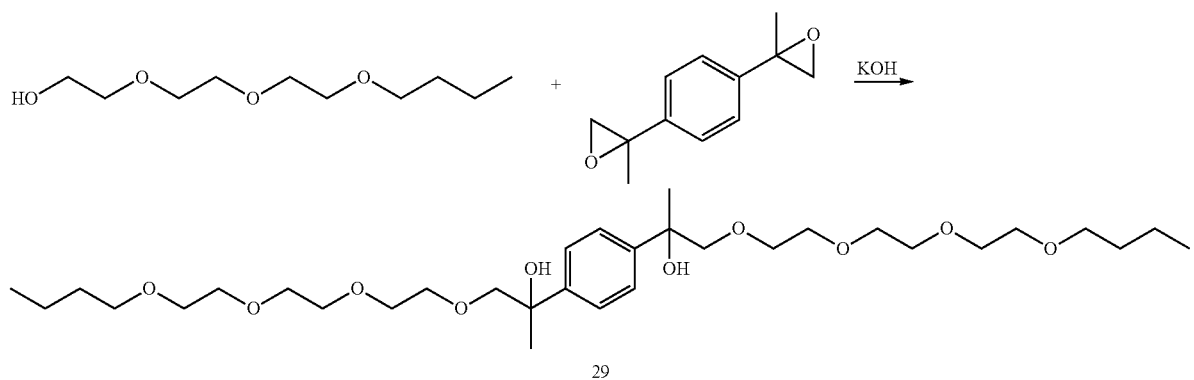
LC-MS $t_R$: 7.54 min (Exact mass: 602.40 m/z, found: 602.4 m/z).
Example 9: Preparation of 2,2'-(1,3-phenylene)bis
(1-((1-((1-methoxypropan-2-yl)oxy)propan-2-yl)oxy)propan-2-ol) [30]
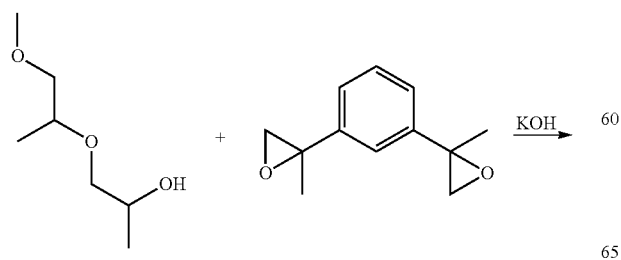
mixture of isomers
-continued
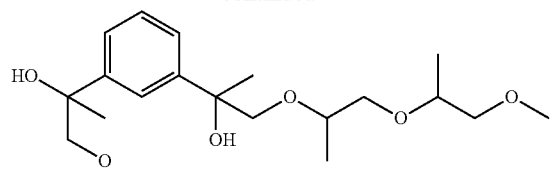
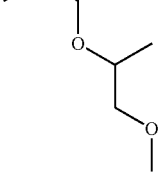
LC-MS $t_R$: 6.40 min (Exact mass: 486.32 m/z, found: 486.3 m/z).

Example 10: Preparation of 2,2'-(1,3-phenylene)bis(1-((1-((1-methoxypropan-2-yl)oxy)propan-2-yl)oxy)propan-2-ol) [31]

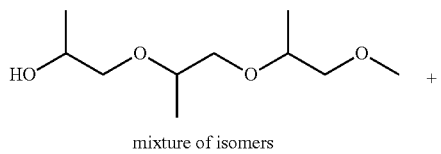

mixture of isomers

+

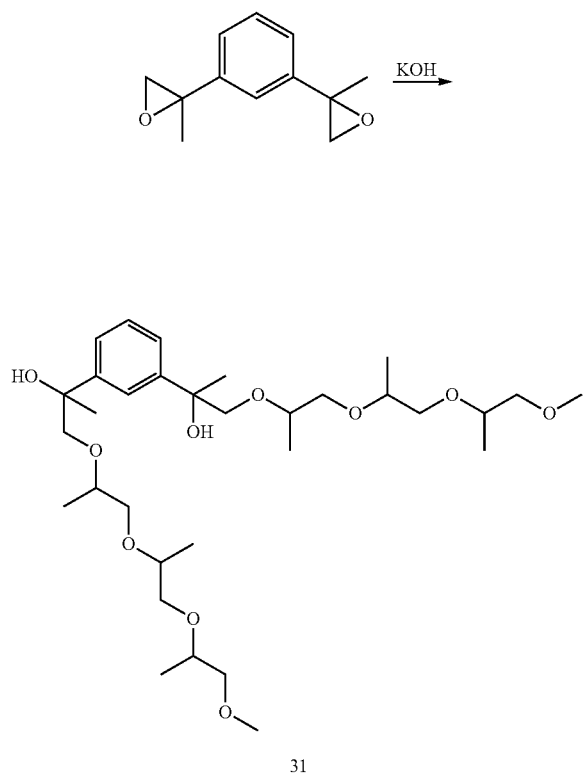

31

LC-MS $t_R$: 7.41 min (Exact mass: 602.40 m/z, found: 602.4 m/z).

Example 11: Preparation of 2,2'-(1,3-phenylene)bis(1-(2-(2-methoxyethoxy)ethoxy)propan-2-ol) [32]

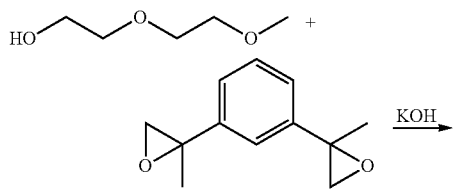

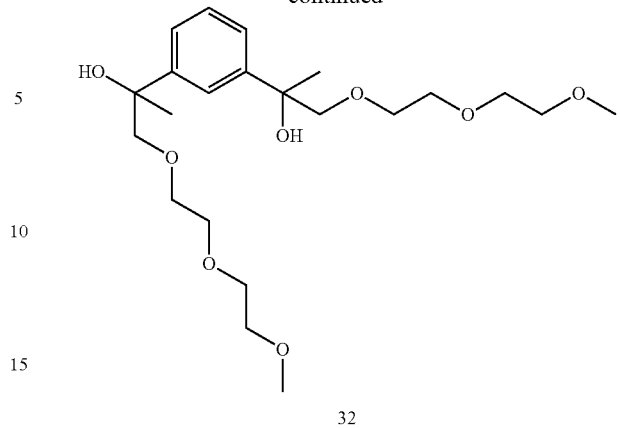

32

LC-MS $t_R$: 4.56 min (Exact mass: 430.26 m/z, found: 430.3 m/z).

Example 12: Preparation of 2,2'-(1,3-phenylene)bis(1-(2-(2-ethoxyethoxy)ethoxy)propan-2-ol) [33]

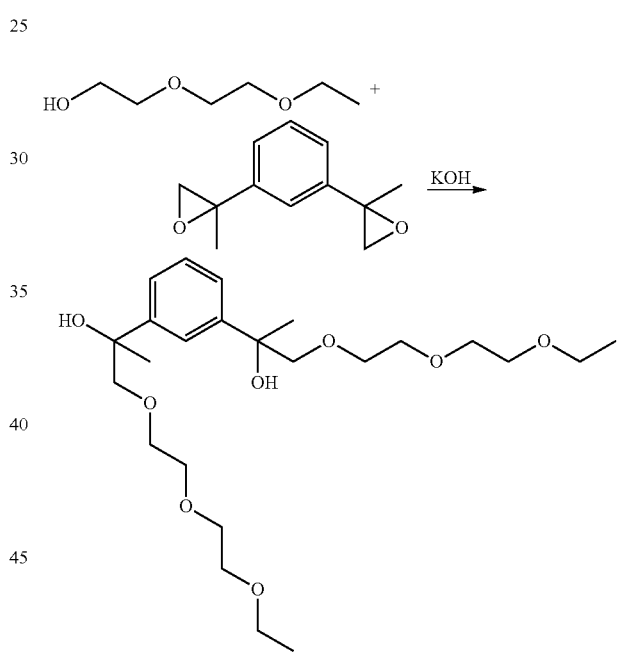

33

LC-MS $t_R$: 5.26 min (Exact mass: 458.29 m/z, found: 458.3 m/z).

Example 13: Preparation of 2,2'-(1,3-phenylene)bis(1-(2-(2-propoxyethoxy)ethoxy)propan-2-ol) [34]

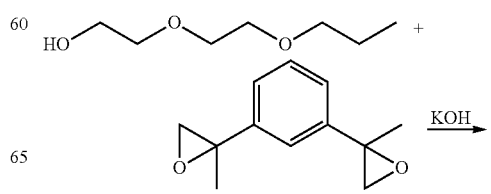

-continued
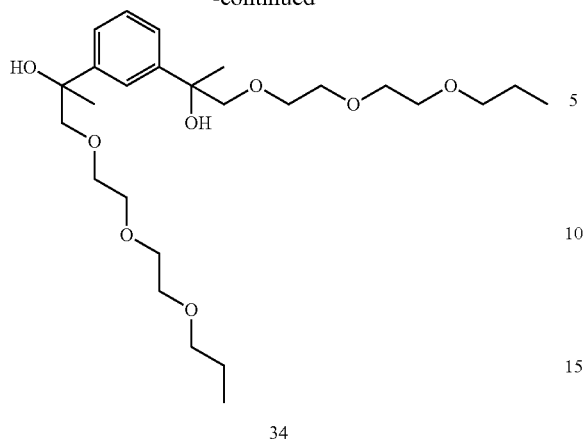
34
LC-MS $t_R$: 6.60 min (Exact mass: 486.32 m/z, found: 486.3 m/z).
Example 14: Preparation of 2,2'-(1,3-phenylene)bis(1-(2-(2-butoxyethoxy)ethoxy)propan-2-ol) [35]
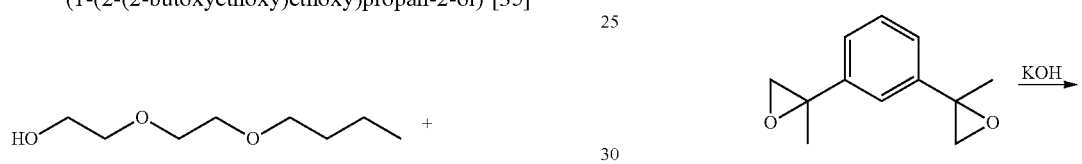
35
LC-MS $t_R$: 7.73 min (Exact mass: 514.35 m/z, found: 514.3 m/z).
Example 15: Preparation of 13,13'-(1,3-phenylene)bis(2,5,8,11-tetraoxatetradecan-13-ol) [36]
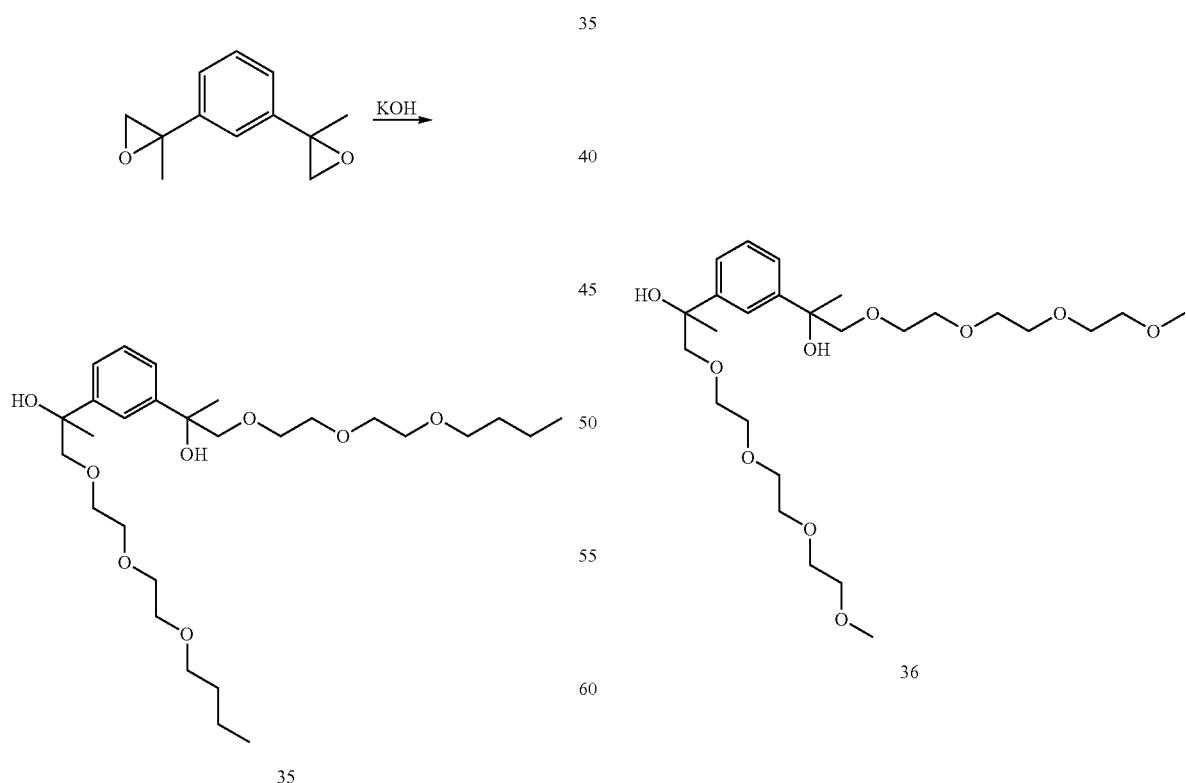
36
LC-MS $t_R$: 4.63 min (Exact mass: 518.31 m/z, found: 518.3 m/z).

Example 16: Preparation of 2,2'-(1,3-phenylene)bis(4,7,10,13-tetraoxaheptadecan-2-ol) [37]

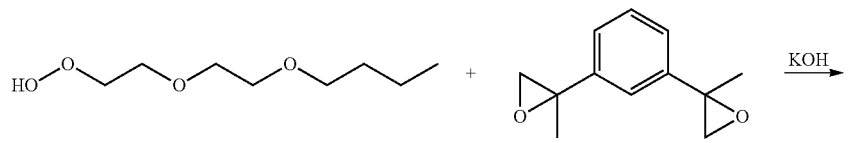

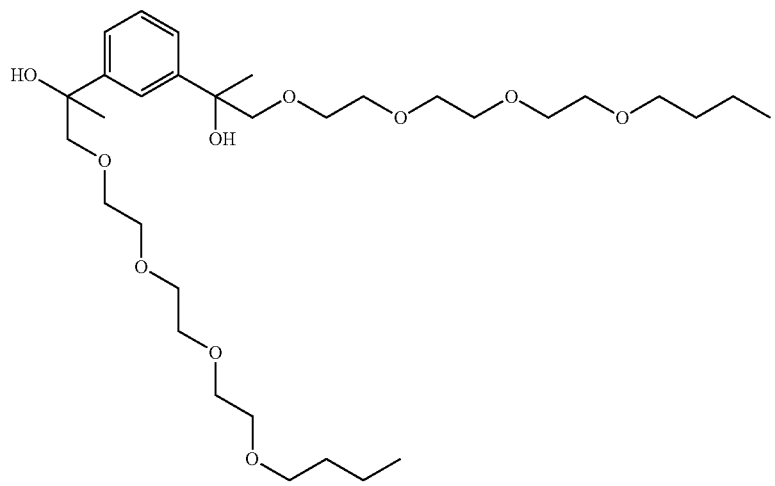

37

LC-MS $t_R$: 7.66 min (Exact mass: 602.40 m/z, found 602.4 m/z).

LC-MS Instrument Conditions (Agilent 1100 LC):
Sample Prep: 2-3 mg/mL in DMSO
Column: Zorbax XDB-C18×4.6 mm, 5 μm
Column Temp: 40° C.
Injection Volume: 2 μL
DAD: 190-600 nm collection
Pump Conditions: Initial—97% water (2.5 mM NH$_4$OAc) (Solvent A) and 3% acetonitrile (Solvent B)
Gradient:

| Time (min) | % Solvent A | % Solvent B | Flow (mL/min) |
|---|---|---|---|
| 0 | 97 | 3 | 1.0 |
| 10 | 0 | 100 | 1.0 |
| 25 | 0 | 100 | 1.0 |
| 25.1 | 97 | 3 | 1.0 |
| 30 | 97 | 3 | 1.0 |

Mass spectra were acquired with a Micromass LCT mass spectrometer, which was coupled to the LC. Mass spectra were collected using electrospray ionization in both the positive-ion and negative ion modes. Ammonium acetate (50 mM in MeOH) was added post column (0.1 mL/min) to enhance ionization efficiency. ES+/ES− scan range was 60-3300 amu (25 and 75V).

General Procedure for Dehydration

To a 4-necked round-bottom flask fitted with an overhead stirrer, thermocouple, and nitrogen inlet was added acetic anhydride (5 equiv.) and sodium bisulfate monohydrate (0.025 equiv.). The mixture was then heated to 65° C. and held for 30 minutes. The dicarbinol was then added dropwise over the course of 4-5 hrs. via a pressure-equalizing addition funnel. Once the addition was complete, the reaction was checked by GC. Once complete, the mix was transferred to a 1-neck round-bottom flask and the excess acetic anhydride/acetic acid was removed under reduced pressure at a temperature range of 45°-65° C., with a vacuum of 20-60 mm Hg using a rotary evaporatory. The crude was taken up in toluene. The organics were then washed with 10% caustic (×2) solution and then 5% ammonium hydroxide solution. The mixture was dried with MgSO4 and simultaneously treated with activated carbon. After filtration, the volatiles were removed under reduced pressure using a rotary evaporator. Light-boiling impurities were removed by distillation. The enol ether/1,1-disubstituted olefin was Kugelrohr-distilled to afford product blends.

Example 17: Preparation of, a mixture of (E,E/Z, Z)—1,4-bis(1-((1-((1-methoxypropan-2-yl)oxy)propan-2-yl)oxy)prop-1-en-2-yl)benzene [6a], (E,Z)-1-(1-((1-((1-methoxypropan-2-yl)oxy)propan-2-yl)oxy)prop-1-en-2-yl)-4-(3-((1-((1-methoxypropan-2-yl)oxy)propan-2-yl)oxy)prop-1-en-2-yl)benzene [6b], and 1,4-bis(3-((1-((1-methoxypropan-2-yl)oxy)propan-2-yl)oxy)prop-1-en-2-yl)benzene [6c]
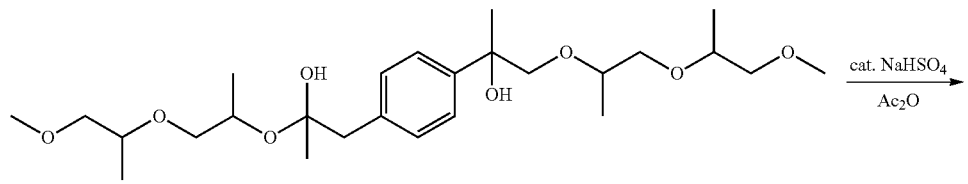
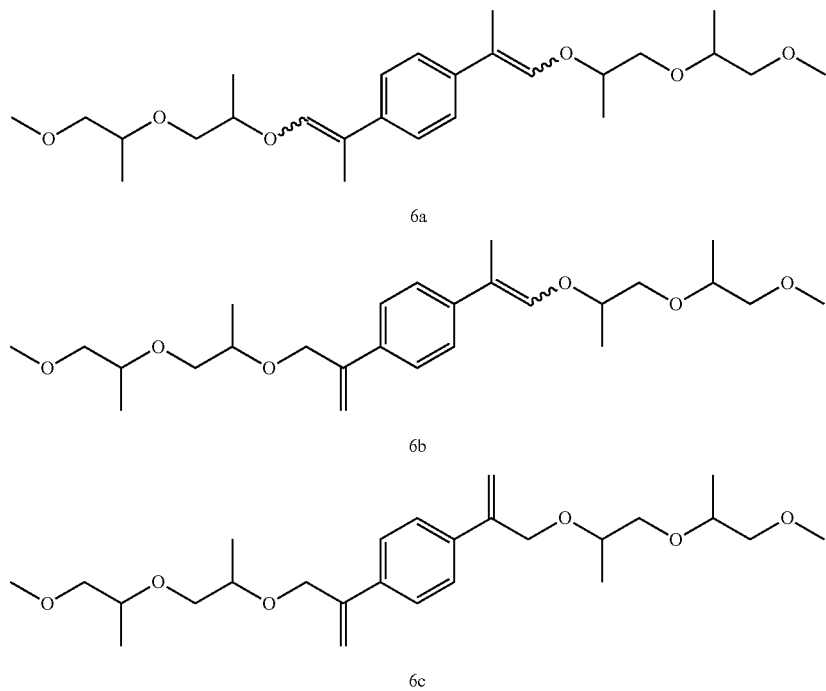
GC-MS $t_R$: 25.80 min, 26.28 min, 26.80 min, 27.30 min, 28.38 min, 28.94 min (Exact mass: 450.30 m/z, found: 450.4 m/z).

Example 18: Preparation of, a mixture of (E,E/Z,Z)-1,4-bis(4,7,10-trimethyl-2,5,8,11-tetraoxatetradec-12-en-13-yl)benzene [7a], (E,Z)-4,7,10-trimethyl-13-(4-(4,7,10-trimethyl-2,5,8,11-tetraoxatetradec-13-en-13-yl)phenyl)-2,5,8,11-tetraoxatetradec-12-ene [7b], and 1,4-bis(4,7,10-trimethyl-2,5,8,11-tetraoxatetradec-13-en-13-yl)benzene [7c]
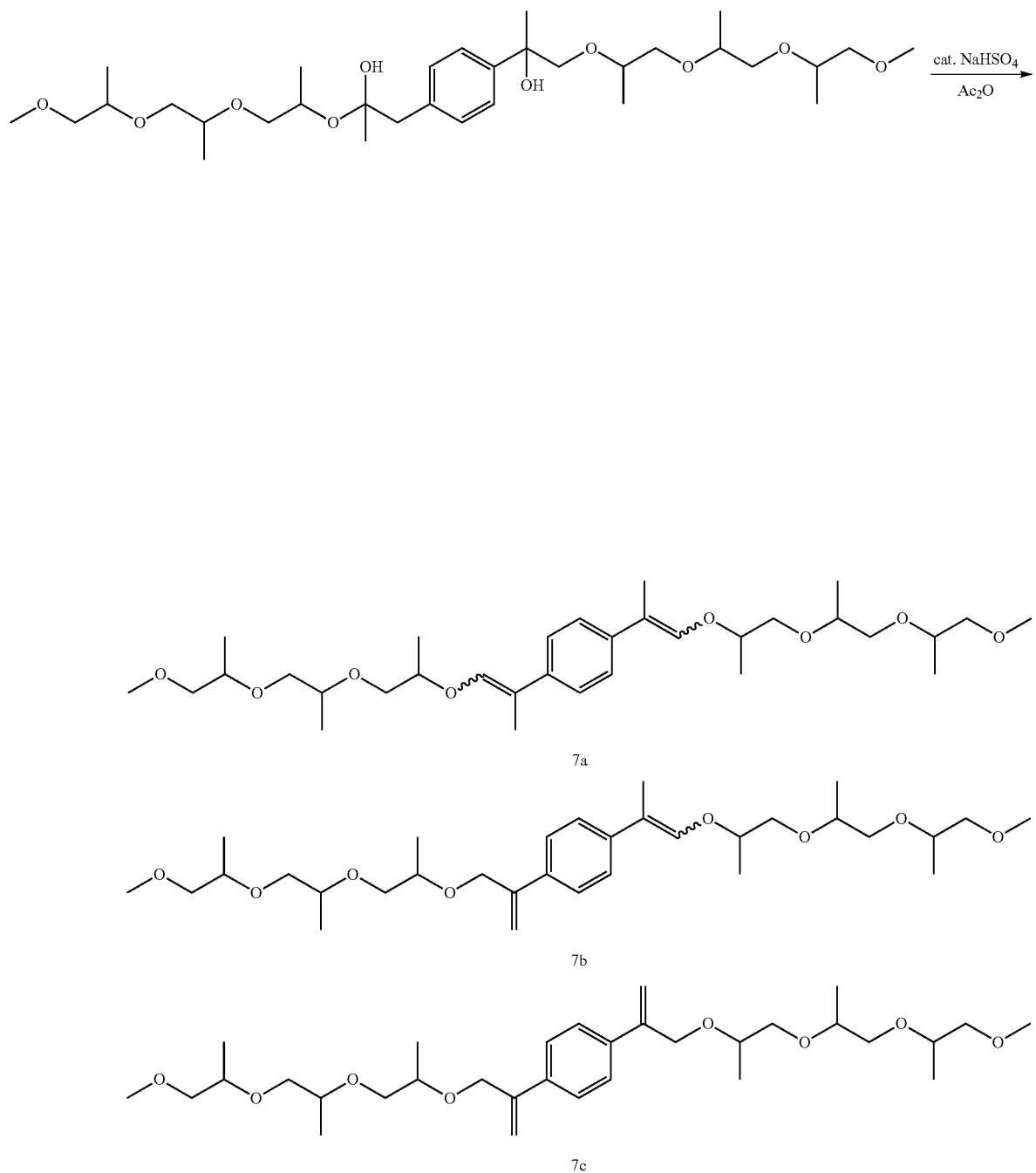
GC-MS $t_R$: 43.08 (broad peak), 69.53 min (broad peak) (Exact mass: 566.38 m/z, found: 566.5 m/z).

Example 19: Preparation of, a mixture of (E,E/Z,Z)-1,4-bis(1-(2-(2-methoxyethoxy)ethoxy)prop-1-en-2-yl)benzene [8a], (E,Z)-1-(1-(2-(2-methoxyethoxy)ethoxy)prop-1-en-2-yl)-4-(3-(2-(2-methoxyethoxy)ethoxy)prop-1-en-2-yl)benzene [8b], and 1,4-bis(3-(2-(2-methoxyethoxy)ethoxy)prop-1-en-2-yl)benzene [8c]
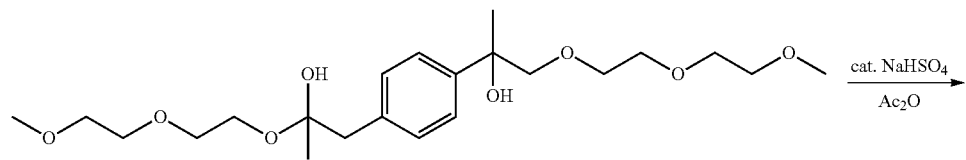
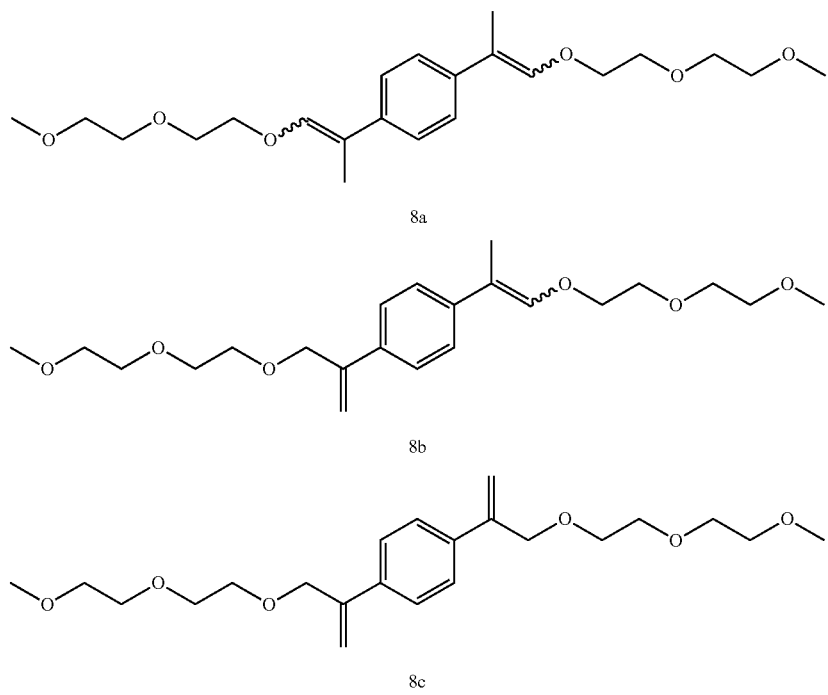
GC-MS $t_R$: 23.9 min, 24.29 min, 24.48 min, 25.64 min, 25.96 min, 27.63 min (Exact mass: 394.24 m/z, found: 394.3 m/z).

Example 20: Preparation of, a mixture of (E,E/Z, Z)-1,4-bis(1-(2-(2-ethoxyethoxy)ethoxy)prop-1-en-2-yl)benzene [9a], (E/Z)-1-(1-(2-(2-ethoxyethoxy)ethoxy)prop-1-en-2-yl)-4-(3-(2-(2-ethoxyethoxy)ethoxy)prop-1-en-2-yl)benzene [9b], and 1,4-bis(3-(2-(2-ethoxyethoxy)ethoxy)prop-1-en-2-yl)benzene [9c]
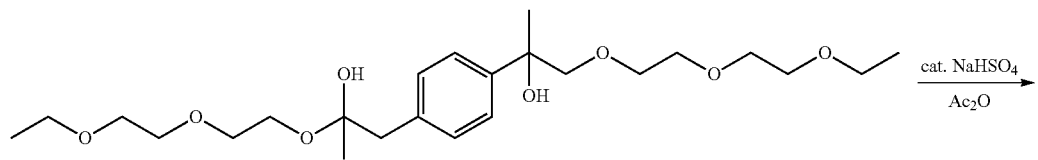
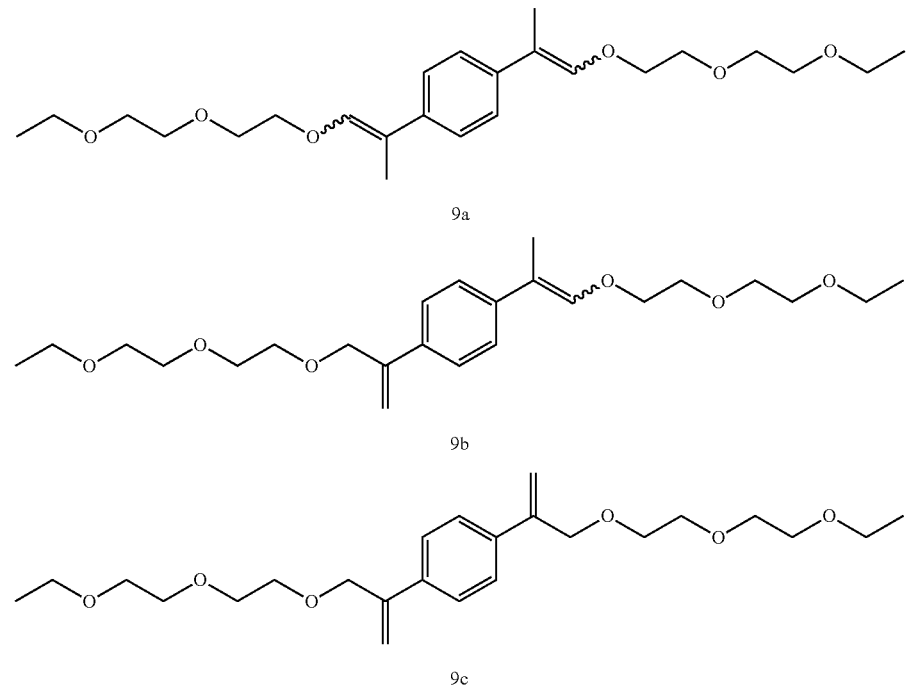
GC-MS $t_R$: 25.64 min, 26.23 min, 26.55 min, 28.00 min, 28.47 min, 30.67 min (Exact mass: 422.27 m/z, found: 422.3 m/z).

Example 21: Preparation of, a mixture of (E,E/Z, Z)-1,4-bis(1-(2-(2-propoxyethoxy)ethoxy)prop-1-en-2-yl)benzene [10a], (E,Z)-1-(1-(2-(2-propoxy-ethoxy)ethoxy)prop-1-en-2-yl)-4-(3-(2-(2-propoxyethoxy)ethoxy)prop-1-en-2-yl)benzene [10b], 1,4-bis(3-(2-(2-propoxyethoxy)ethoxy)prop-1-en-2-yl)benzene [10c]
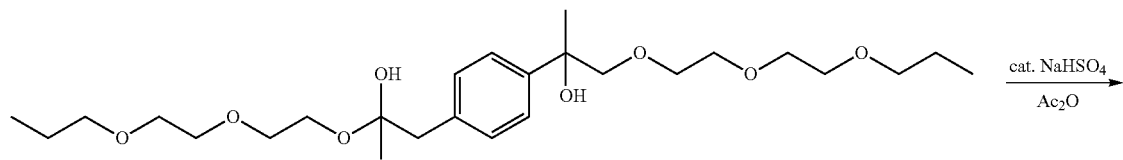
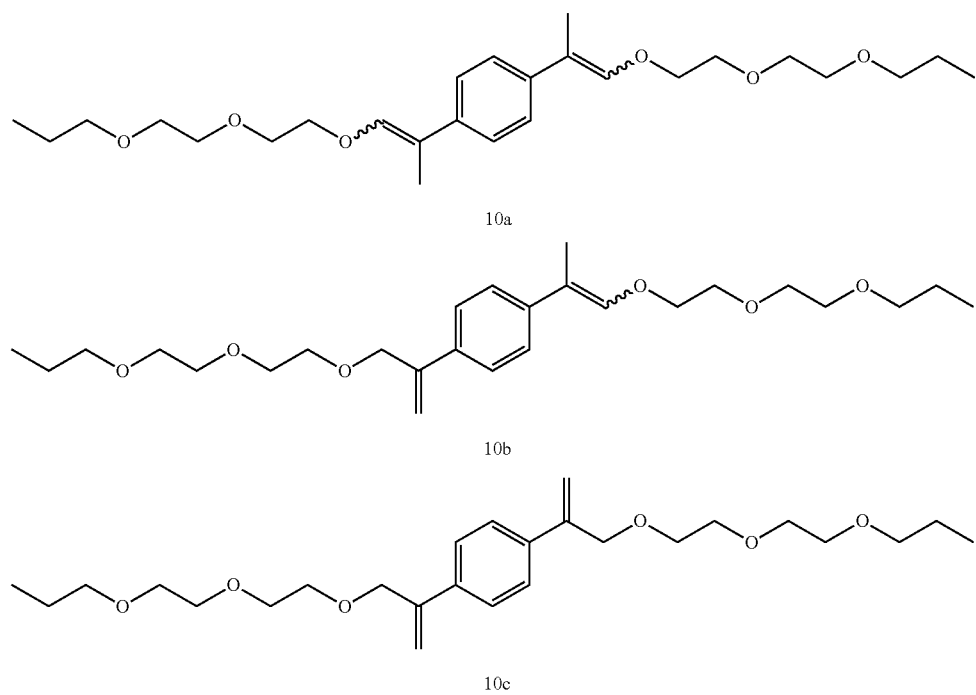
GC-MS $t_R$: 29.70 min, 30.67 min, 31.30 min, 33.27 min, 34.18 min, 37.58 min (Exact mass: 450.30 m/z, found: 450.3 m/z).

Example 22: Preparation of, a mixture of (E,E/Z,Z)-1,4-bis(1-(2-(2-butoxyethoxy)ethoxy)prop-1-en-2-yl)benzene [11a], (E,Z)-1-(1-(2-(2-butoxyethoxy)ethoxy)prop-1-en-2-yl)-4-(3-(2-(2-butoxyethoxy)ethoxy)prop-1-en-2-yl)benzene [11b], 1,4-bis(3-(2-(2-butoxyethoxy)ethoxy)prop-1-en-2-yl)benzene [11c]
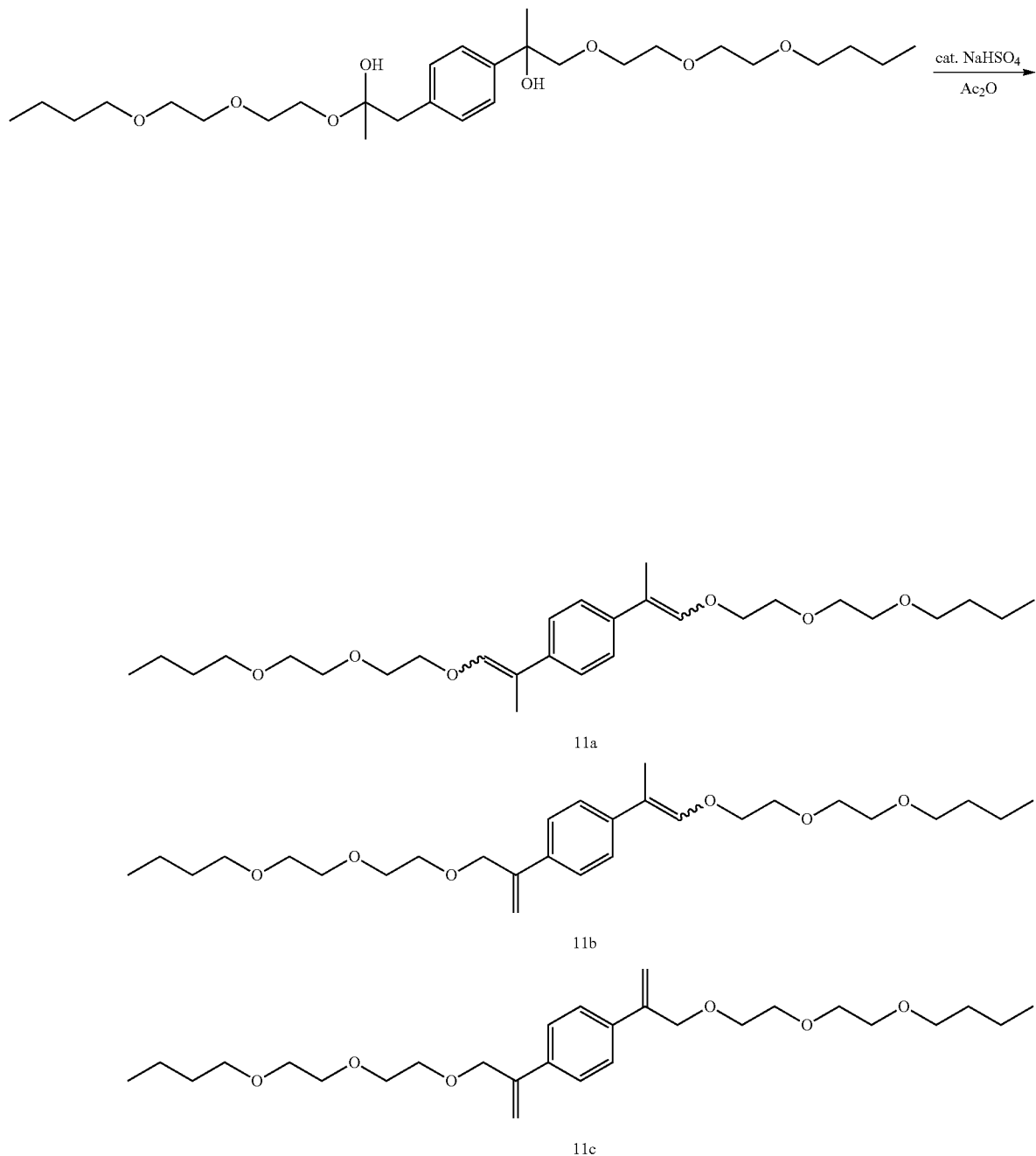
GC-MS $t_R$: 36.07 min, 37.71 min, 38.86 min, 41.45 min (Exact mass: 478.33 m/z, found: 478.4 m/z).

Example 23: Preparation of, a mixture of (E,E/Z,Z)-1,4-di(2,5,8,11-tetraoxatetradec-12-en-13-yl)benzene [12a], (E,Z)-13-(4-(2,5,8,11-tetraoxatetradec-13-en-13-yl)phenyl)-2,5,8,11-tetraoxatetradec-12-ene [12b], and 1,4-di(2,5,8,11-tetraoxatetradec-13-en-13-yl)benzene [12c]
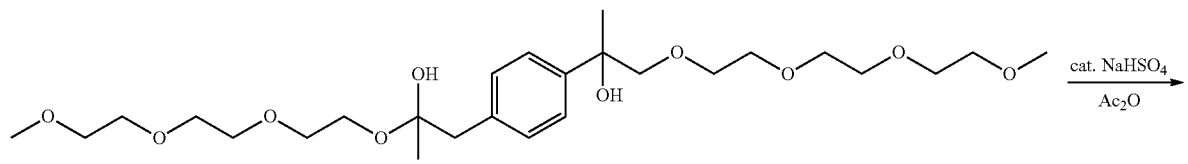
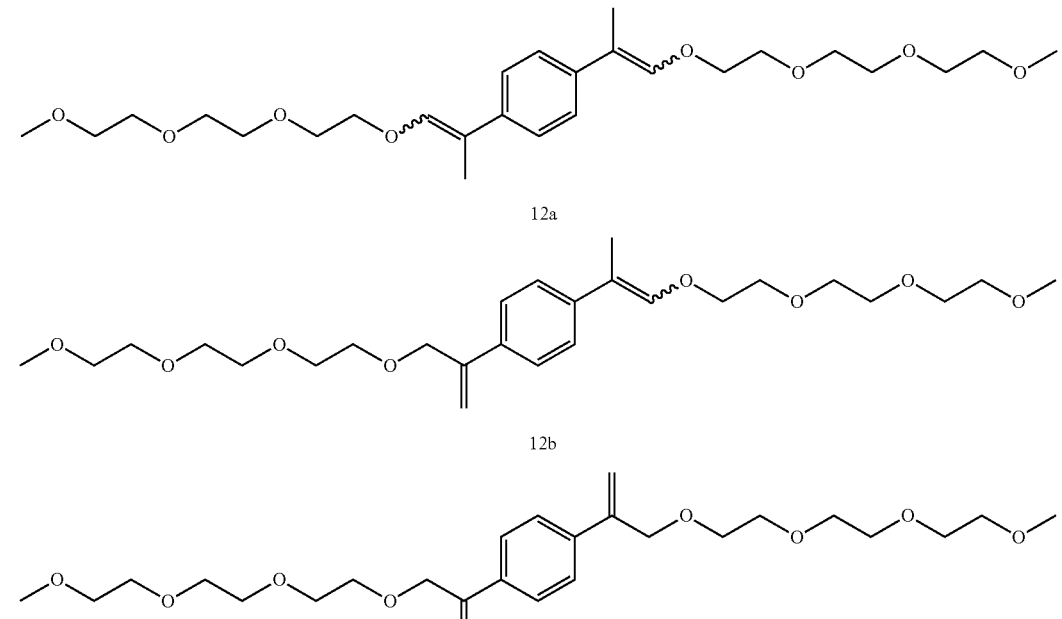
GC-MS $t_R$: 39.51 min, 41.51 min, 42.78 min, 46.43 min, 48.26 min, 55.04 min (Exact mass: 482.29 m/z, found: 482.4 m/z).

Example 24: Preparation of, a mixture of (E,E/Z, Z)-1,3-bis(1-((1-((1-methoxypropan-2-yl)oxy)propan-2-yl)oxy)prop-1-en-2-yl)benzene [13a], (E/Z)-1-(1-((1-((1-methoxypropan-2-yl)oxy)propan-2-yl)oxy)prop-1-en-2-yl)-3-(3-((1-((1-methoxypropan-2-yl)oxy)propan-2-yl)oxy)prop-1-en-2-yl)benzene [13b], and 1,3-bis(3-((1-((1-methoxypropan-2-yl)oxy)propan-2-yl)oxy)prop-1-en-2-yl)benzene [13c]
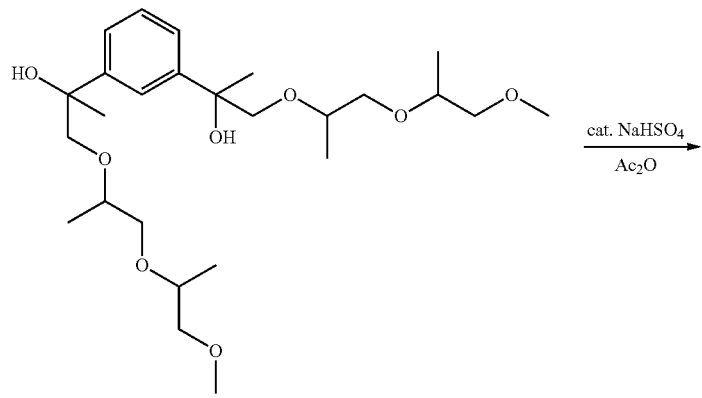
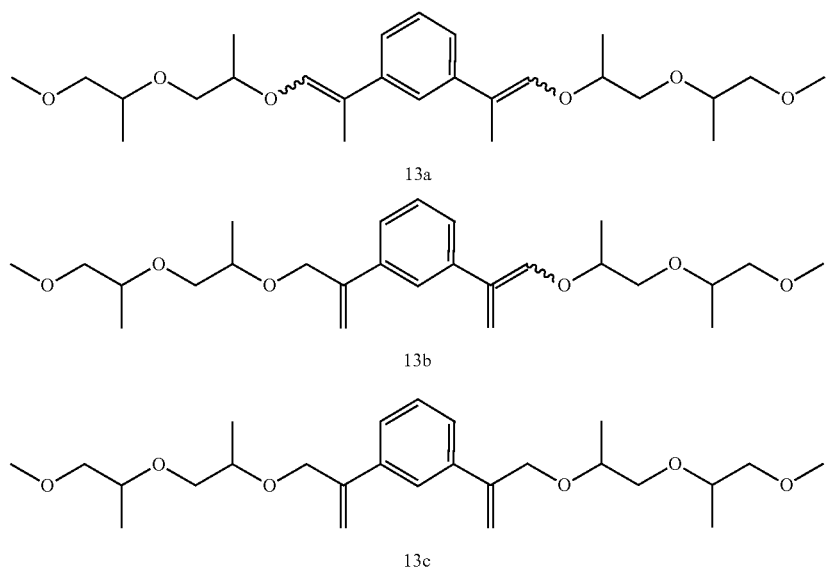
GC-MS $t_R$: 22.78 min, 23.14 min, 23.45 min, 23.91 min, 24.27 min, 24.59 min, 25.17 min, 25.58 min, 26.05 min (Exact mass: 450.30 m/z, found: 450.4 m/z).

Example 25: Preparation of, a mixture of (E,E/Z,Z)-1,3-bis(4,7,10-trimethyl-2,5,8,11-tetraoxatetradec-12-en-13-yl)benzene [14a], (E/Z)-4,7,10-trimethyl-13-(3-(4,7,10-trimethyl-2,5,8,11-tetraoxatetradec-13-en-13-yl)phenyl)-2,5,8,11-tetraoxatetradec-12-ene [14b], and 1,3-bis(4,7,10-trimethyl-2,5,8,11-tetraoxatetradec-13-en-13-yl)benzene [14c]
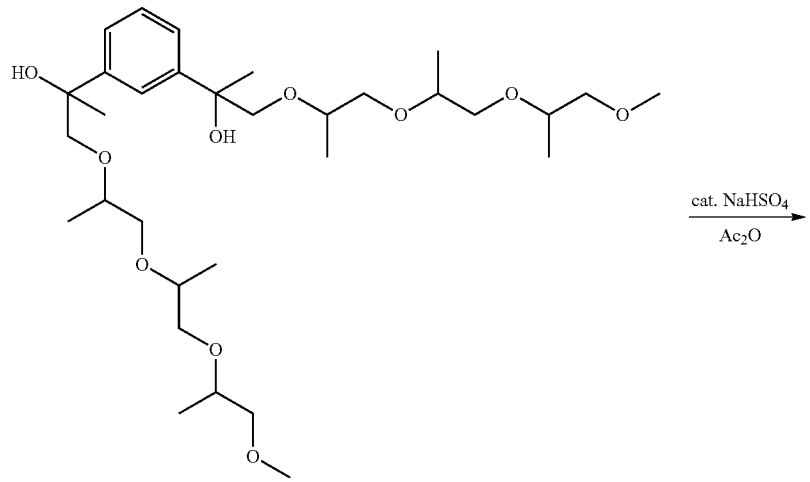
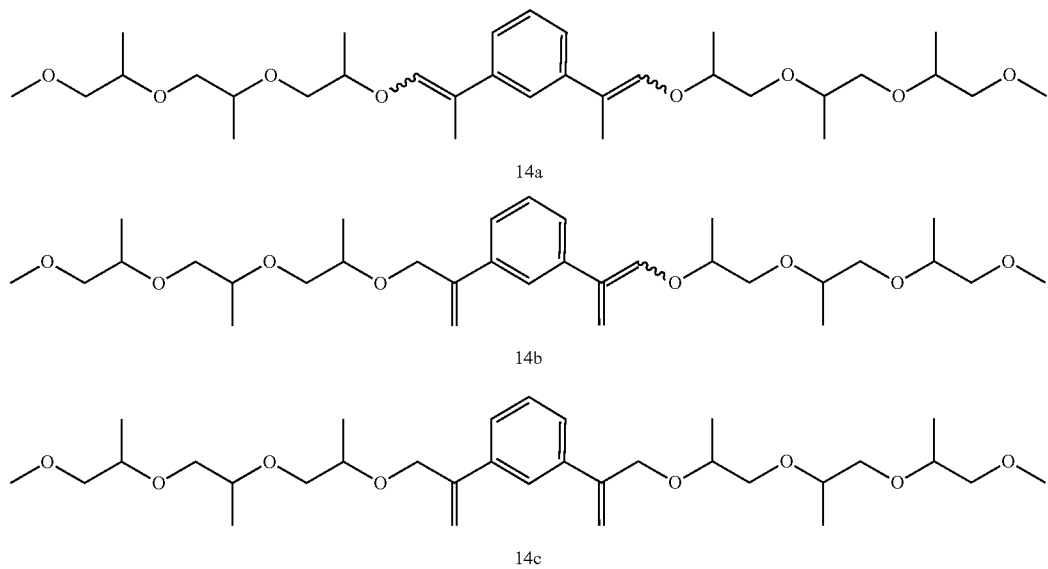
GC-MS $t_R$: 41.84-43.72 min (broad peak) (Exact mass: 566.38 m/z, found: 566.5 m/z).

Example 26: Preparation of, a mixture of (E,E/Z, Z)-1,3-bis(1-(2-(2-methoxyethoxy)ethoxy)prop-1-en-2-yl)benzene [15a], (E/Z)-1-(1-(2-(2-methoxyethoxy)ethoxy)prop-1-en-2-yl)-3-(3-(2-(2-methoxyethoxy)ethoxy)prop-1-en-2-yl)benzene [15b], 1,3-bis(3-(2-(2-methoxyethoxy)ethoxy)prop-1-en-2-yl)benzene [15c]
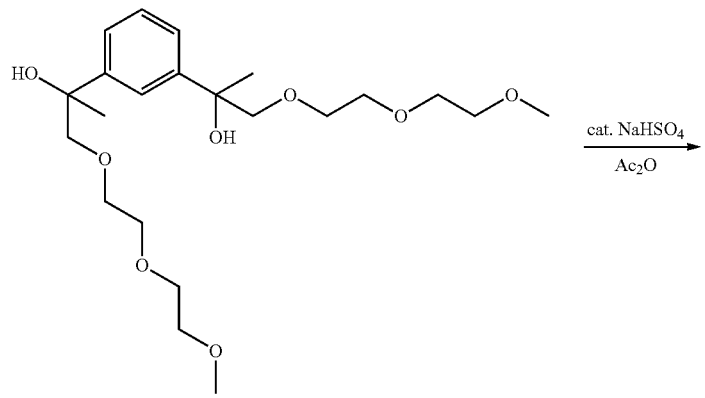
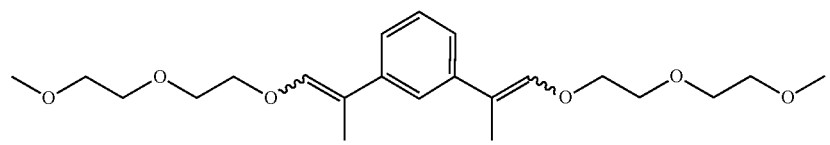
15a
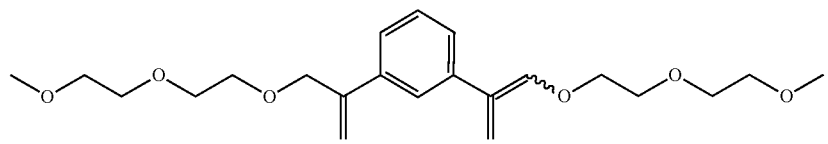
15b
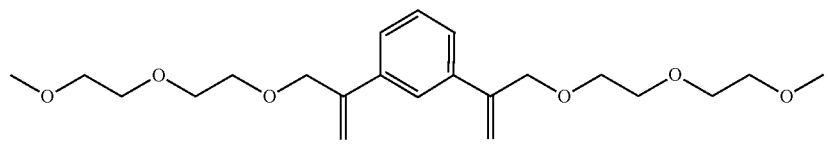
15c
GC-MS $t_R$: 22.57 min, 22.91 min, 23.08 min, 23.79 min, 24.08 min, 25.43 min (Exact mass: 394.24 m/z, found: 394.3 m/z).

Example 27-1 and Example 27-2: Preparation of a Mixture of (E,E/Z,Z)-1,3-bis(1-(2-(2-ethoxyethoxy)ethoxy)prop-1-en-2-yl)benzene [16a], (E/Z)-1-(1-(2-(2-ethoxyethoxy)ethoxy)prop-1-en-2-yl)-3-(3-(2-(2-ethoxyethoxy)ethoxy)prop-1-en-2-yl)benzene [16b], and 1,3-bis(3-(2-(2-ethoxyethoxy)ethoxy)prop-1-en-2-yl)benzene [16c]

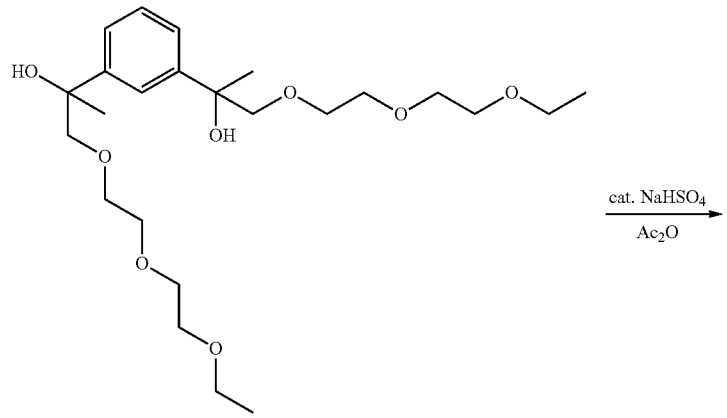

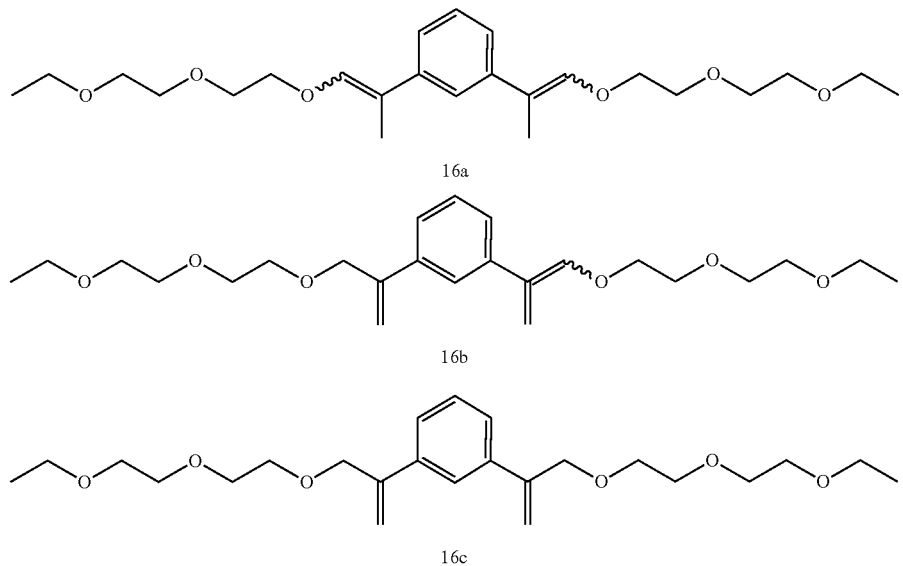

GC-MS $t_R$: 24.07 min, 24.73 min, 24.80 min, 25.72 min, 25.87 min, 27.78 min (Exact mass: 422.27 m/z, found: 422.3 m/z).

Example 27-1: 0.025 equiv. of sodium bisulfate used. Ratio of 16a:16b:16c=1.0:1.7:3.6.

Example 27-2: 0.50 equiv. of sodium bisulfate used. Ratio of 16a:16b:16c=1.0:2.7:10.

Example 28: Preparation of a mixture of (E,E/Z,Z)-1,3-bis(1-(2-(2-propoxyethoxy)ethoxy)prop-1-en-2-yl)benzene [17a], (E/Z)-1-(1-(2-(2-propoxyethoxy)ethoxy)prop-1-en-2-yl)-3-(3-(2-(2-propoxyethoxy)ethoxy)prop-1-en-2-yl)benzene [17b], and 1,3-bis(3-(2-(2-propoxyethoxy)ethoxy)prop-1-en-2-yl)benzene [17c]
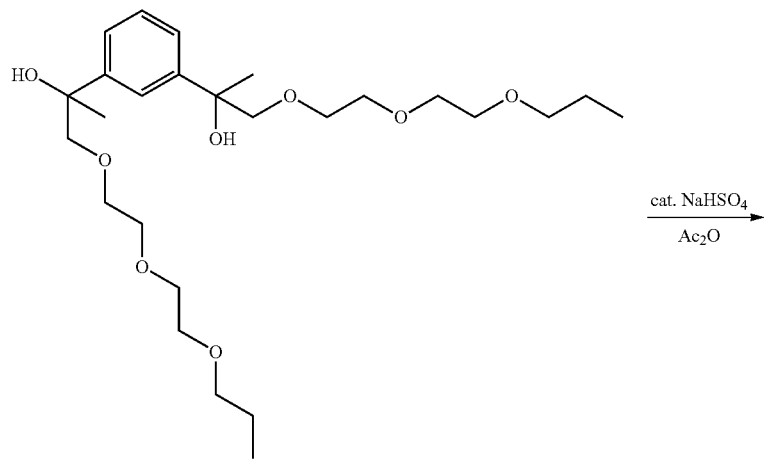
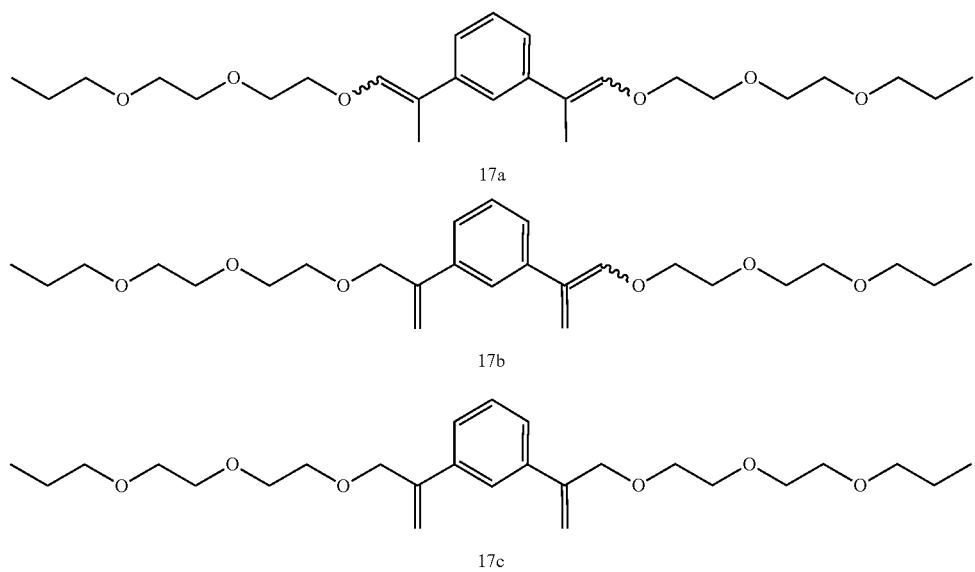
GC-MS $t_R$: 27.42 min, 28.16 min, 28.63 min, 29.80 min, 30.61 min, 33.20 min (Exact mass: 450.30 m/z, found: 450.4 m/z).

Example 29: Preparation of a mixture of (E,E/Z,Z)-1,3-bis(1-(2-(2-butoxyethoxy)ethoxy)prop-1-en-2-yl)benzene [18a], (E/Z)-1-(1-(2-(2-butoxyethoxy)ethoxy)prop-1-en-2-yl)-3-(3-(2-(2-butoxyethoxy)ethoxy)prop-1-en-2-yl)benzene [18b], and 1,3-bis(3-(2-(2-butoxyethoxy)ethoxy)prop-1-en-2-yl)benzene [18c]
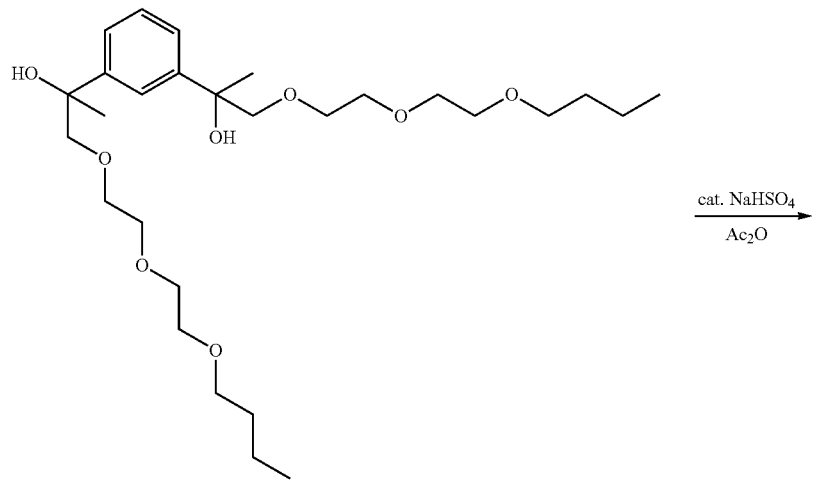
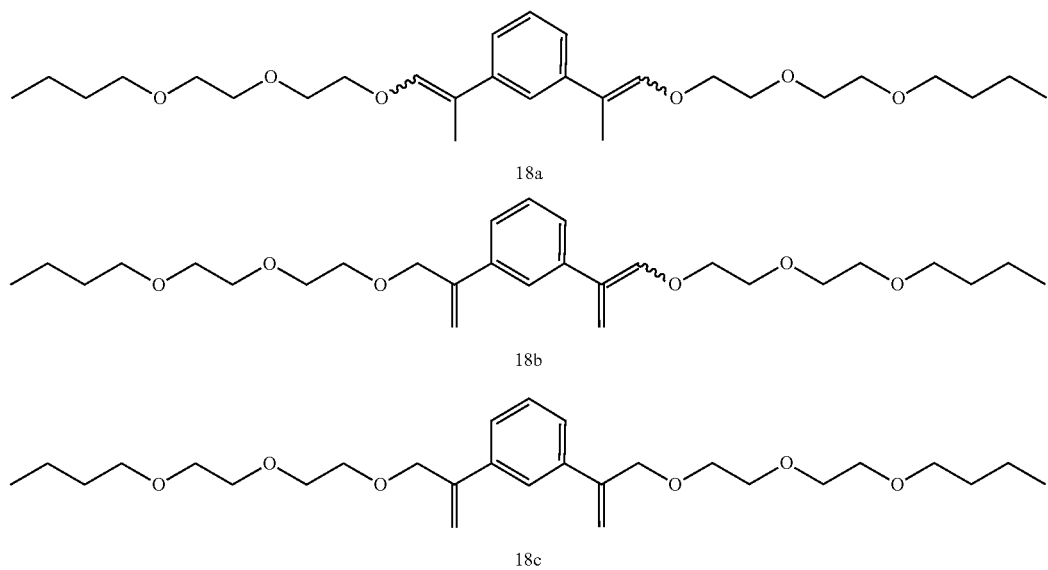
GC-MS $t_R$: 32.75 min, 33.89 min, 34.68 min, 36.20 min, 37.42 min, 41.29 min (Exact mass: 478.33 m/z, found: 478.4 m/z).

Example 30: Preparation of a mixture of (E,E/Z,Z)-1,3-di(2,5,8,11-tetraoxatetradec-12-en-13-yl)benzene [19a], (E/Z)-13-(3-(2,5,8,11-tetraoxatetradec-13-en-13-yl)phenyl)-2,5,8,11-tetraoxatetradec-12-ene [19b], and 1,3-di(2,5,8,11-tetraoxatetradec-13-en-13-yl)benzene [19c]

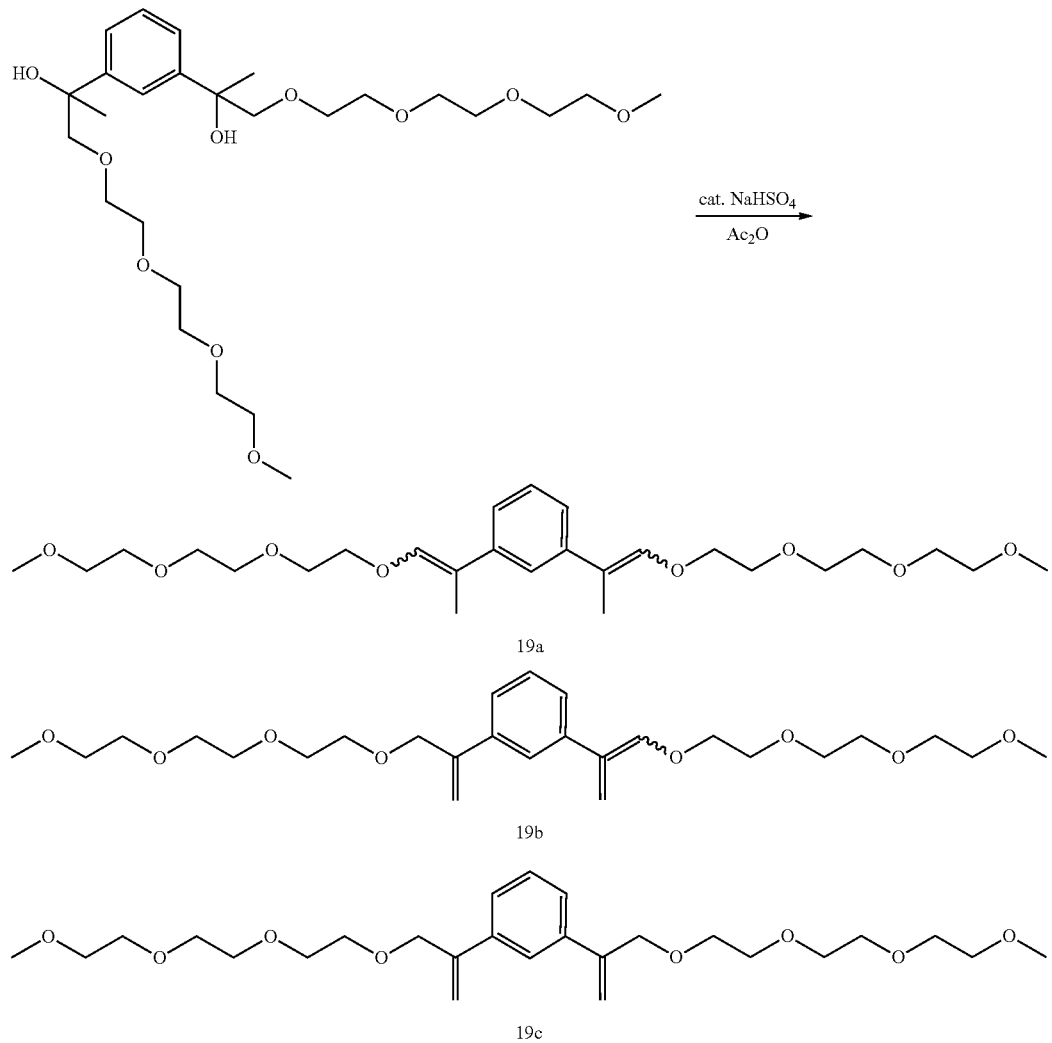

GC-MS $t_R$: 35.57 min, 36.92 min, 37.81 min, 39.66 min, 41.11 min, 45.59 min (Exact mass: 482.29 m/z, found: 482.3 m/z).

Instrument Parameters—Agilent 6890N GC with Agilent 5975B VL MSD

Sample Prep: 100 μL sample diluted to 1 mL with toluene; Column: DB-5 30 m×0.25 mm×0.25 μm; Oven Ramp: 0-4.5 mins at 40° C.; Ramp 20 C/min to 280 C, Hold 53.5 mins; Injector: Temperature—250° C.; Split Flow—65 mL/min; Carrier Flow Rate—1.3 mL/min; Volume—1.0 μL; MS: Transfer Line—280° C.; Ion Source Temp—230° C.; Mass Range—34-700 amu. Methyl palmitate $t_R$=16.6 min using the above method.

Conditions—Agilent 1100 LC
Sample Prep: 2-3 mg/mL in DMSO
Column A: Zorbax XDB-C18×4.6 mm, 5 μm
Column B: Poroshell EC-C18 50×4.6 mm, 2.7 μm
Column Temp: 40° C.
Injection Volume: 2 μL
DAD: 190-600 nm collection
Pump Conditions: Initial—97% water (2.5 mM NH$_4$OAc) (Solvent A) and 3% acetonitrile (Solvent B)

Gradient:

| Time (min) | % Solvent A | % Solvent B | Flow (mL/min) |
|---|---|---|---|
| 0 | 97 | 3 | 1.0 |
| 10 | 0 | 100 | 1.0 |
| 25 | 0 | 100 | 1.0 |
| 25.1 | 97 | 3 | 1.0 |
| 30 | 97 | 3 | 1.0 |

Mass spectra were acquired with a Micromass LCT mass spectrometer, which was coupled to the LC. Mass spectra were collected using electrospray ionization in both the positive-ion and negative ion modes. Ammonium acetate (50 mM in MeOH) was added post column (0.1 mL/min) to enhance ionization efficiency. ES+/ES− scan range was 60-3300 amu (25 and 75V).

The invention has been described in detail with reference to the embodiments disclosed herein, but it will be understood that variations and modifications can be effected within the spirit and scope of the invention.

I claim:

1. A method of making aromatic enol ethers comprising:
   a) contacting a glycol ether with a di-epoxide in the presence of a base to form a first reaction product;
   b) combining said first reaction product with an aromatic hydrocarbon and an acid to form a second reaction product having an aqueous phase and a non-aqueous phase;
   c) separating said second reaction product aqueous phase from said second reaction product non-aqueous second phase;
   d) drying said second reaction product non-aqueous phase to recover a dicarbinol;
   e) dehydrating said dicarbinol with an acid catalyst to form a mixture of an aromatic enol ether and water; and
   f) separating said aromatic ether from said water.

2. The method of claim 1, step a) wherein said glycol ether is ethylene glycol monomethyl ether, ethylenene glycol monoethyl ether, ethylene glycol monopropyl ether, ethylene glycol monobutyl ether, diethylene glycol monomethyl ether, diethylene glycol monoethyl ether, diethylene glycol monopropyl ether, diethylene glycol monoisopropyl ether, diethylene glycol monobutyl ether, triethylene glycol monomethyl ether, triethylene glycol monoethyl ether, triethylene glycol monopropyl ether, triethylene glycol monobutyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, dipropylene glycol monopropyl ether, dipropylene glycol monobutyl ether, tripropylene glycol monomethyl ether, tripropylene glycol monoethyl ether, tripropylene glycol monopropyl ether, tripropylene glycol monobutyl ether or mixtures thereof.

3. The method of claim 1, step a) wherein said di-epoxide is 1,3-bis(2-methyloxiran-2-yl)benzene, 1,4-bis(2-methyloxiran-2-yl)benzene, 1,3-di(oxiran-2-yl)benzene, 1,4-di(oxiran-2-yl)benzene 4,4'-bis(2-methyloxiran-2-yl)-1,1'-biphenyl, 2,6-bis(2-methyloxiran-2-yl)naphthalene or mixtures thereof.

4. The method of claim 1, step a) wherein said base is sodium hydroxide, potassium hydroxide, lithium hydroxide, sodium metal, sodium methoxide, potassium tert-butoxide, anion exchange resins and mixtures and combinations thereof.

5. The method of claim 1, step b) wherein said aromatic hydrocarbon is toluene, chlorobenzene, para-xylene, meta-xylene, ortho-xylene or mixtures thereof.

6. The method of claim 1, step b) wherein said acid is a cationic exchange resin, sulfuric acid, phosphoric acid, hydrochloric acid, formic acid, acetic acid and combinations and mixtures thereof.

7. The method of claim 1 wherein in said separation step c) is a liquid-liquid extraction.

8. The method of claim 1 wherein in said drying step d) is filtration through a desiccant bed, azeotropic distillation with heptane, toluene, or xylene or combinations thereof.

9. The method of claim 1, step e) wherein said acid catalysts is para-toluene sulfonic acid, methane sulfonic acid, camphor sulfonic acid, a cationic exchange resin, sulfuric acid, phosphoric acid, hydrochloric acid, formic acid, chloroacetic acid, dichloroacetic acid, trichloroacetic acid, trifluoroacetic acid, sodium hydrogen sulfate, potassium hydrogen sulfate and mixtures and combinations thereof.

* * * * *